US009446050B2

(12) United States Patent
Bueno et al.

(10) Patent No.: US 9,446,050 B2
(45) Date of Patent: Sep. 20, 2016

(54) METHOD FOR TREATMENT OF MESOTHELIOMA

(71) Applicant: THE BRIGHAM AND WOMEN'S HOSPITAL, INC., Boston, MA (US)

(72) Inventors: Raphael Bueno, Brookline, MA (US); David Sugarbaker, Milton, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 14/353,925

(22) PCT Filed: Oct. 24, 2012

(86) PCT No.: PCT/US2012/061514
§ 371 (c)(1),
(2) Date: Apr. 24, 2014

(87) PCT Pub. No.: WO2013/062984
PCT Pub. Date: May 2, 2013

(65) Prior Publication Data
US 2014/0294993 A1    Oct. 2, 2014

Related U.S. Application Data

(60) Provisional application No. 61/550,747, filed on Oct. 24, 2011, provisional application No. 61/551,058, filed on Oct. 25, 2011.

(51) Int. Cl.
| | |
|---|---|
| *A61K 31/565* | (2006.01) |
| *A61K 31/519* | (2006.01) |
| *A61K 33/24* | (2006.01) |
| *A61K 31/282* | (2006.01) |
| *G01N 33/68* | (2006.01) |
| *C12Q 1/68* | (2006.01) |
| *A61K 31/566* | (2006.01) |
| *A61K 31/567* | (2006.01) |
| *A61K 45/06* | (2006.01) |
| *A61K 31/555* | (2006.01) |
| *A61K 31/56* | (2006.01) |
| *A61K 31/58* | (2006.01) |
| *G01N 33/574* | (2006.01) |
| *G06F 19/00* | (2011.01) |

(52) U.S. Cl.
CPC ........... *A61K 31/565* (2013.01); *A61K 31/282* (2013.01); *A61K 31/519* (2013.01); *A61K 31/555* (2013.01); *A61K 31/56* (2013.01); *A61K 31/566* (2013.01); *A61K 31/567* (2013.01); *A61K 31/58* (2013.01); *A61K 33/24* (2013.01); *A61K 45/06* (2013.01); *C12Q 1/686* (2013.01); *C12Q 1/6886* (2013.01); *G01N 33/57407* (2013.01); *G01N 33/6872* (2013.01); *G06F 19/34* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 7,622,260 B2 | 11/2009 | Gordon et al. |
| 2011/0059854 A1 | 3/2011 | Gordon et al. |
| 2011/0105855 A1 | 5/2011 | Johnson |

FOREIGN PATENT DOCUMENTS

| | | |
|---|---|---|
| EP | 0147155 A2 | 7/1985 |
| JP | 2010279311 A | 12/2010 |
| WO | 2007133957 A1 | 11/2007 |
| WO | 2009147658 A2 | 12/2009 |

OTHER PUBLICATIONS

Pinton et al. in Cancer Research 69(11), 4598-4604 (2009).*
Coleman et al. in Journal of the American College of Surgeons (213(3) Supplement, p. S38 (2011).*
Pinton et al. in Cancer Research 2009; 69(11) 4598-4604 (2009).*
Coleman et al. in Journal of the American College of Surgeons, Sep. 2011, vol. 213, Issue 3, Supplement, p. S38.*
Mesothelioma.com at https://web.archive.org/web/20101029051747/http://www.mesothelioma.com/treatment/conventional/chemotherapy/cisplatin.htm.(retrieved from the internet on Aug. 8, 2015).*
Moos et al. in Drug Devleopment Research 70:1-21 (2009).*
Papendorp et al. in Journal of Cell Physiology 125(3):591-595 (1985) (Abstract).*
Ivanov, S.V. et al., Int J Cancer 124(3):589-599 (Feb. 1, 2009). doi: 10.1002/ijc.23949. "Genomic events associated with progression of pleural malignant mesothelioma."
Krimpenfort, P. et al., Nature 448(7156):943-946 (Aug. 23, 2007). "p15Ink4b is a critical tumour suppressor in the absence of p16Ink4a."
Nakano, Environ Health Prev Med, 13(2):75-83 (Mar. 2008). doi: 10.1007/s12199-007-0016-7. Epub Feb. 28, 2008 "Current therapies for malignant pleural mesothelioma."
Ruas, M. et al., Biochim Biophys Acta, 1378(2):F115-177 (Oct. 14, 1998). "The p16INK4a/CDKN2A tumor suppressor and its relatives."
Sugarbaker, D.J. et al., PNAS 105(9):3521-3526 (Mar. 4, 2008). "Transcriptome sequencing of malignant pleural mesothelioma tumors."

(Continued)

*Primary Examiner* — Dennis Heyer
(74) *Attorney, Agent, or Firm* — Nixon Peabody LLP; David S. Resnick; Tari W. Mills

(57) ABSTRACT

The present invention provides that Ras-like, estrogen-regulated, growth inhibitor (RERG) is a malignant mesothelioma biomarker of clinical course and treatment sensitivity and, itself a target for mesothelioma treatment. A low RERG level in a mesothelioma subject indicates poor prognosis. Analyzing RERG expression level along can help mesothelioma patients make treatment choices. Furthermore, mesothelioma can be treated by modulating RERG activity, for example, with treatment with estrogen or estrogen-like agents.

23 Claims, 11 Drawing Sheets

(56) References Cited

OTHER PUBLICATIONS

Yang, H. et al. Curr Treat Options Oncol. Jun. 2008;9(2-3):147-57. doi: 10.1007/s11864-008-0067-z. Epub Aug. 15, 2008. "Mesothelioma epidemiology, carcinogenesis, and pathogenesis."

Coleman, M.H. et al., Journal of the American College of Surgeons, Sep. 2011, vol. 213, Issue 3, Supplement, p. S38. "Association of mesothelioma outcome with RERG expression."

De Rienzo A., Clin Cancer Res. 17(2):310-316 (Jan. 15, 2011). doi: 10.1158/1078-0432.CCR-10-0806. Epub Nov. 18, 2010. "Fine-needle aspiration biopsies for gene expression ratio-based diagnostic and prognostic tests in malignant pleural mesothelioma."

Pinton G. et al., Cancer Res.69(11):4598-4604 (Jun. 1, 2009). doi: 10.1158/0008-5472.CAN-08-4523. "Estrogen receptor-beta affects the prognosis of human malignant mesothelioma."

Wang A.G. et al., J Korean Med Sci. 21(5):891-896 (Oct. 2006). "Expression of the RERG gene is gender-dependent in hepatocellular carcinoma and regulated by histone deacetyltransferases."

* cited by examiner

SEQUENCE LISTING

<160> NUMBER OF SEQ ID NOS: 4

<210> SEQ ID NO 1
<211> LENGTH: 2325
<212> TYPE: DNA
<213> ORGANISM: Homo sapiens

<400> SEQUENCE: 1

```
actgcagcat cctggccgct gagcgcagcg gccttggccg ggctcagctc gcgtcctgcc      60
gcagtccctc cgccgctagt cggagcgagc gcgagtgagg agaccccgc cgggccactg     120 gcacttgctt ctgcggcgag tcccacccac gaccgcagcc cagcaactcg caaacgcaac    180
ctgaagcctg ggctgcgcag tgtgggaggg cttcgcgatc ttgggggacc cattccgaac    240
ttgcagagga ccgtagctct cctggcctgg agagtgtgaa caggattgtg gactcttcca    300
agattcacaa tgatatggtg aatccaaaga ctggaaccaa aaagatttac tcagtgcttt    360
agttttaaca acagtaaatt gtctaccaac acccatcatg gctaaaagtg cggaggtcaa    420
actggcaata tttgggagag caggcgtggg caagtcagct cttgtagtga gatttctgac    480
caaacggttc atctgggaat atgatcccac cctcgaatca acctaccgac accaagcaac    540
catcgatgat gaagttgttt ccatggagat actagacact gctggtcagg aagataccat    600
tcagagggag gggcacatgc gatgggggga aggctttgtg ctggtctacg acattactga    660
ccgaggaagt tttgaggaag tgctgccact taagaacatc ctagatgaga tcaaaaagcc    720
caagaatgtg actctcatct tggttggaaa caaagctgac ttggaccact ccaggcaggt    780
tagcacagaa gaaggagaga gctggccac agaattggct tgtgcttttt acgagtgctc    840
tgcctgcact ggagaaggga acatcacaga gatattctat gaattgtgtc gagaggtgcg    900
tcgccggagc atggtgcagg caagacgag gcgacgcagc tccaccacgc atgtcaagca    960
agccattaac aagatgctca ccaaaatcag tagttaggca gcccagctga ggtggaccaa   1020
ctaattggaa acactcttcc ccttctgttc cccctttcaaa aataaaacaa atattgcat   1080 tctttgtttg gattctgaga aatgtctggg cttcccattg tttctggcct ctaataggtt   1140
gggaagtttt agcgtgtttt atgcaatttc agtgctaaca atttcttcct ttcctgcttg   1200
aataagatac actctaatgg catttgaaca tgtaatcacc agagattctg aaatgactgg   1260
```

```
tttatgttaa gctatttttta ggcatcttca ccttgcttta agtaggttga agttttttgca      1320 aaggcattta aaaattcaat ttcttgtcag atactacaaa taattttctt aaaagtctaa      1380
gatagcagaa aatacagtaa aaacacagga gaagaagctg agctattgga acaggaaata      1440
gaaggaactc tagtttctgt ttgaagtgag attttctga attatctaat atcatctagg       1500
ttttctttaa aattttattt tgttcttcag ttcaagcatc ttctcactaa tgttttttcac     1560 tataacagag aattcatttc aatttgagtt ggttctctca atgatctatt gatcattaca      1620
ccctaactct ccttccttgg ctcaaacaat attttcccta taacaaaggc aataggacac      1680
aaaattcaca tcctgctggg ccttttttca tcaagtcagg gtgatataaa aacattggaa      1740
gtcttttcac caaaccctga ctttattgaa tgctagtaga agatgtagaa ttagagacat      1800
ctgatttgtt tatcacctta gcagaaaaac cacagtccaa aagacaagca aattaagaat     1860
ggagcttaac catgcctcca ttgggaagtc tagactttga gccaggtaca gtaagaaaaa      1920
ttagcctctg attcattaag tttgccacat gacttatttt gatattttgg atacattaac    1980
tcacttagga gaattcagaa aagaatgggt gattaaagtt cattacagct gaataaatgt    2040
gtctaaaaca gactcttgta ttctgaaagt acagtctaca actgataaaa ccttatgatt      2100
cttttctccc ccattatgcc cctatatata tcaagatttg ggtactttat tttagtagaa      2160
aatatatatc ttttacatat gtatgtattt ataaatgcat agatatatgt ataaaaattt   2220
gtaagcgtta gcggcattaa ttcaccaatg catttgaca acttgatgta actgacttta      2280
ttttatgtga ctataataaa aagcataatt ttctcattct gtcat                     2325
```

<210> SEQ ID NO 2
<211> LENGTH: 2268
<212> TYPE: DNA
<213> ORGANISM: Homo sapiens

<400> SEQUENCE: 2

```
actgcagcat cctggccgct gagcgcagcg gccttggccg ggctcagctc gcgtcctgcc       60
gcagtccctc cgccgctagt cggagcgagc gcgagtgagg agaccccgc cgggccactg      120 gcacttgctt ctgcggcgag tcccacccac gaccgcagcc cagcaactcg caaacgcaac     180
ctgaagcctg ggctgcgcag tgtgggaggg cttcgcgatc ttgggggacc cattccgaac    240
ttgcagagga ccgtagctct cctggcctgg agagtgtgaa caggattgtg gactcttcca       300
agattcacaa tgatatggtg aatccaaaga ctggaaccaa aaagatttac tcagtgcttt      360
agttttaaca acagtaaatt gtctaccaac acccatcatg gctaaaagtg cggaggtcaa      420
actggcaata tttgggagag caggcgtggg caagtcagaa tcaacctacc gacaccaagc      480
aaccatcgat gatgaagttg tttccatgga gatactagac actgctggtc aggaagatac     540
cattcagagg gaggggcaca tgcgatgggg ggaaggcttt gtgctggtct acgacattac      600
tgaccgagga agttttgagg aagtgctgcc acttaagaac atcctagatg agatcaaaaa     660
gcccaagaat gtgactctca tcttggttgg aaacaaagct gacttggacc actccaggca     720
ggttagcaca gaagaaggag agaagctggc cacagaattg gcttgtgctt tttacgagtg      780
ctctgcctgc actggagaag gaacatcac agagatattc tatgaattgt gtcgagaggt       840
gcgtcgccgg aggatggtgc agggcaagac gaggcgacgc agctccacca cgcatgtcaa      900
gcaagccatt aacaagatgc tcaccaaaat cagtagttag gcagcccagc tgaggtggac      960
caactaattg gaaacactct tccccttctg ttccccttc aaaaataaaa caaaatattg      1020
cattctttgt ttggattctg agaaatgtct gggcttccca ttgtttctgg cctctaatag    1080
```

```
gttgggaagt tttagcgtgt tttatgcaat tcagtgcta acaatttctt cctttcctgc    1140
ttgaataaga tacactctaa tggcatttga acatgtaatc accagagatt ctgaaatgac    1200
tggtttatgt taagctattt ttaggcatct tcaccttgct ttaagtaggt tgaagttttt    1260
gcaaaggcat ttaaaaattc aatttcttgt cagatactac aaataatttt cttaaaagtc    1320
taagatagca gaaaatacag taaaaacaca ggagaagaag ctgagctatt ggaacaggaa    1380
atagaaggaa ctctagtttc tgtttgaagt gaggattttc tgaattatct aatatcatct    1440
aggttttctt taaaatttta ttttgttctt cagttcaagc atcttctcac taatgttttt    1500
cactataaca gagaattcat ttcaatttga gttggttctc tcaatgatct attgatcatt    1560
acaccctaac tctccttcct tggctcaaac aatattttcc ctataacaaa ggcaatagga    1620
cacaaaattc acatcctgct gggcctttt tcatcaagtc agggtgatat aaaaacattg    1680
gaagtctttt caccaaaccc tgactttatt gaatgctagt agaagatgta gaattagaga    1740
catctgattt gttatcacc ttagcagaaa aaccacagtc caaaagacaa gcaaattaag    1800
aatggagctt aaccatgcct ccattgggaa gtctagactt tgagccaggt acagtaagaa    1860
aaattagcct ctgattcatt aagtttgcca catgacttat tttgatattt tggatacatt    1920
aactcactta ggagaattca gaaagaatg ggtgattaaa gttcattaca gctgaataaa    1980
tgtgtctaaa acagactctt gtattctgaa agtacagtct acaactgata aaaccttatg    2040
attcttttct cccccattat gcccctatat atatcaagat ttgggtactt tatttagta    2100 gaaaatatat atcttttaca tatgtatgta tttataaatg catagatata tgtataaaaa    2160
tttgtaagcg ttagcggcat taattccacc atgcatttgg acaacttgat gtaactgact    2220
ttattttatg tgactataat aaaaagcata attttctcat tctgtcat                 2268
```

<210> SEQ ID NO 3
<211> LENGTH: 199
<212> TYPE: PRT
<213> ORGANISM: Homo sapiens

<400> SEQUENCE: 3

```
Met Ala Lys Ser Ala Glu Val Lys Leu Ala Ile Phe Gly Arg Ala Gly
1               5                   10                  15

Val Gly Lys Ser Ala Leu Val Val Arg Phe Leu Thr Lys Arg Phe Ile
            20                  25                  30

Trp Glu Tyr Asp Pro Thr Leu Glu Ser Thr Tyr Arg His Gln Ala Thr
        35                  40                  45

Ile Asp Asp Glu Val Val Ser Met Glu Ile Leu Asp Thr Ala Gly Gln
    50                  55                  60

Glu Asp Thr Ile Gln Arg Glu Gly His Met Arg Trp Gly Glu Gly Phe
65                  70                  75                  80

Val Leu Val Tyr Asp Ile Thr Asp Arg Gly Ser Phe Glu Glu Val Leu
                85                  90                  95

Pro Leu Lys Asn Ile Leu Asp Glu Ile Lys Lys Pro Lys Asn Val Thr
            100                 105                 110

Leu Ile Leu Val Gly Asn Lys Ala Asp Leu Asp His Ser Arg Gln Val
        115                 120                 125

Ser Thr Glu Glu Gly Glu Lys Leu Ala Thr Glu Leu Ala Cys Ala Phe
    130                 135                 140

Tyr Glu Cys Ser Ala Cys Thr Gly Glu Gly Asn Ile Thr Glu Ile Phe
145                 150                 155                 160
```

```
Tyr Glu Leu Cys Arg Glu Val Arg Arg Arg Met Val Gln Gly Lys
                165             170             175

Thr Arg Arg Arg Ser Ser Thr Thr His Val Lys Gln Ala Ile Asn Lys
            180             185             190

Met Leu Thr Lys Ile Ser Ser
        195

<210> SEQ ID NO 4
<211> LENGTH: 180
<212> TYPE: PRT
<213> ORGANISM: Homo sapiens

<400> SEQUENCE: 4

Met Ala Lys Ser Ala Glu Val Lys Leu Ala Ile Phe Gly Arg Ala Gly
1               5                   10                  15

Val Gly Lys Ser Glu Ser Thr Tyr Arg His Gln Ala Thr Ile Asp Asp
            20                  25                  30

Glu Val Val Ser Met Glu Ile Leu Asp Thr Ala Gly Gln Glu Asp Thr
        35                  40                  45

Ile Gln Arg Glu Gly His Met Arg Trp Gly Glu Gly Phe Val Leu Val
    50                  55                  60

Tyr Asp Ile Thr Asp Arg Gly Ser Phe Glu Glu Val Leu Pro Leu Lys
65                  70                  75                  80

Asn Ile Leu Asp Glu Ile Lys Lys Pro Lys Asn Val Thr Leu Ile Leu
                85                  90                  95

Val Gly Asn Lys Ala Asp Leu Asp His Ser Arg Gln Val Ser Thr Glu
            100                 105                 110

Glu Gly Glu Lys Leu Ala Thr Glu Leu Ala Cys Ala Phe Tyr Glu Cys
        115                 120                 125

Ser Ala Cys Thr Gly Glu Gly Asn Ile Thr Glu Ile Phe Tyr Glu Leu
    130                 135                 140

Cys Arg Glu Val Arg Arg Arg Met Val Gln Gly Lys Thr Arg Arg
145                 150                 155                 160

Arg Ser Ser Thr Thr His Val Lys Gln Ala Ile Asn Lys Met Leu Thr
                165                 170                 175

Lys Ile Ser Ser
            180
```

METHOD FOR TREATMENT OF MESOTHELIOMA

CROSS REFERENCE TO RELATED APPLICATIONS

This application is a 35 U.S.C. §371 National Stage Application of International Application No. PCT/US2012/061514 filed on Oct. 24, 2012, which designates the United States, and which claims benefit under 35 U.S.C. §119(e) of U.S. Provisional Application No. 61/550,747 filed on Oct. 24, 2011 and U.S. Provisional Application No. 61/551,058 filed on Oct. 25, 2011, the contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 18, 2014, is named 20140424_SequenceListing_TextFile_043214_075771_US and is 10 KB in size.

FIELD OF THE INVENTION

The invention relates to methods for the treatment of mesothelioma and assays for predicting prognosis of mesothelioma and assays and systems for determining therapeutic responsiveness of the subject to the treatment of mesothelioma using estrogen, or an estrogen elevating compound.

BACKGROUND OF THE INVENTION

Mesothelioma is a tumor that occurs in the mesothelium that covers the surface of the pleura, peritoneum and pericardium that respectively envelop the organs of the chest cavity such as the lungs and heart, and abdominal organs such as the digestive tract and liver. In the case of diffuse pleural mesothelioma, chest pain is caused by invasion of the intercostal nerves on the side of the chest wall pleura, and respiratory and circulatory disorders may occur due to tumor growth and accumulation of pleural fluid in the pleura on the organ side (Takagi, Journal of Clinical and Experimental Medicine, (March Supplement), "Respiratory Diseases", pp. 469-472, 1999). Eventually, there is proliferation into the adjacent mediastinal organs, progressing to direct invasion of the heart or development in the abdominal cavity by means of the diaphragm, or there may be development outside the chest cavity as a result of additional lymphatic or circulatory metastasis.

In the U.S., diffuse pleural mesothelioma is reported to occur in 3,000 persons annually, with the number of cases increasing significantly through the 1980's. The disease is frequently observed in men in their sixties, with the incidence in men being roughly five times that in women. According to recent reports in the U.S. and Europe, the incidence of mesothelioma demonstrates a rapidly increasing trend, and, based on epidemiological statistics from the U.K. in 1995, the number of deaths from mesothelioma is predicted to continue to increase over the next 25 years. In the worst possible scenario, mesothelioma may be found to account for 1% of all deaths among men born in the 1940's.

Numerous different classification schemes for the clinical disease stages have been established for mesothelioma, and since the classification methods differ, comparison of the results of treatment for mesothelioma is difficult (Nakano, Environ Health Prev Med, 2008; 13:75-83).

In addition, malignant mesothelioma (MM) has a causative relationship with exposure to asbestos, and this has also been demonstrated in animal experiments (Tada, Journal of Clinical and Experimental Medicine (March Supplement), "Respiratory Diseases", pp. 406-408, 1999). Asbestos that has been inhaled into the respiratory tract reaches a location directly beneath the pleura where a tumor eventually develops due to chronic irritation for typically 20 years, and this tumor spreads in a thin layer over the entire surface of the pleura. Consequently, although malignant mesothelioma is classified as an asbestos-related disease, not all malignant mesothelioma is caused by asbestos, and well-documented exposure is only observed in about half of all patients.

Malignant pleural mesothelioma (MPM) is resistant to treatment, is associated with an extremely poor prognosis, and requires that countermeasures be taken immediately (Nakano, Respiration, Vol. 18, No. 9, pp. 916-925, 1999). For example, although the folic acid antagonist, methotrexate (MTX), has a satisfactory efficacy rate of 37% in large-dose single treatment in combination with leucovin, its use has not proliferated due to the technical difficulty associated with application to mesothelioma that causes retention of a large amount of pleural fluid (Nakano, Journal of Clinical and Experimental Medicine (March Supplement), "Respiratory Diseases", pp. 570-573, 2003). In addition, although pleuropulmonary excision and pleurectomy are performed for diffuse pleural mesothelioma, there is increased susceptibility to relapse following treatment, and the post-surgical local relapse rate in particular is high at 35-43% (Takagi, Journal of Clinical and Experimental Medicine (March Supplement), "Respiratory Diseases", pp. 469-472, 1999).

The prognosis for malignant mesothelioma is influenced by the stage of the disease. Surgery, when performed as part of a multimodality therapy with cytotoxic chemotherapy and radiation therapy, as well as adjuvant immunological treatments (e.g., interferon or interleukin) can be an effective treatment, but only in the rare event of diagnosis at an early stage.

The incidence of mesothelioma worldwide is increasing and only a minority of patients can benefit from a surgical resection. For patients who are not amenable to curative resection, median overall survival is around 6-7 months. Therapeutic options are limited. Most patients, either treated or untreated, die of complications from local disease. Marketed chemotherapeutic agents, as a single agent or in combination, did not prove able to significantly impact survival.

In mesothelioma, the 9p21.3 deletions are often homozygous and linked with poor prognosis (Ivanov et al., Int J Cancer 2009; 124:589-599). Two tumor suppressor genes are localized in this area: CDKN2A (cyclin-dependent kinase inhibitor), which encodes the cell cycle inhibitory p16$^{INK4A}$ and p14$^{ARF}$ proteins, and the adjacent CDKN2B (p15.sup.INK4B) (Ruas and Peters, Biochim Biophys Acta 1998; 1378:F115-177). Combined deficiency of these products may have a synergistic effect in malignant transformation (Krimpenfort et al., Nature 2007; 448:943-946).

Much emphasis has been placed on the discovery and characterization of a unique tumor marker. However, no marker has yet been identified that has adequate sensitivity or specificity to be clinically useful, although a combination of multiple markers has been shown to increase prognostic accuracy. There is an unmet need for identification of specific and accurate markers associated with mesothelioma, especially those which could have prognostic significance in determining the type and extent of therapy necessary or reasonable for survival, and for compositions which could be employed in treating mesothelioma.

Therefore, a clinically applicable assay directed to a truly predictive biomarker is needed in order to aid in accurately diagnosing subjects and stratifying the risk faced by those subjects. Such an assay would also assist in identifying the survival prognosis of subjects as well as predicting therapeutic responsiveness to specific therapies and treatments.

SUMMARY OF THE INVENTION

Described herein are methods of treatment of mesothelioma and assays and systems directed to determining the prognosis of a subject with mesothelioma and for predicting the therapeutic responsiveness of the subject to treatment.

Described herein are compositions and methods for the treatment and diagnosis of mesothelioma, and determination of prognosis of mesothelioma patients after surgical operation. Specifically, the invention relates to use of Ras-like estrogen-regulated, growth inhibitor (RERG) as a biomarker for mesothelioma and can be used for diagnosis and determination of prognosis of mesothelioma, as well as various treatment of subjects with elevated RERG with estrogen or estrogen-like molecules, (e.g., agents which elevate estrogen or an estrogen mimetic).

As disclosed in the Examples herein, the inventors surprisingly discovered that when the survival or longevity of a population of subjects with mesothelioma is assessed, approximately the top 50% longest surviving subjects had increased expression of RERG as compared to the remaining population (e.g., the 50% with the shortest survival). In particular, the top half (e.g., the cohort of subjects with the longest survival) always did significantly better, and had a better prognosis, and longer overall survival time than the bottom half. This was particularly apparent in female subjects with mesothelioma. Accordingly, the inventors have discovered that female subjects with an expression level of RERG at or above a reference level have a median prolonged life of approximately 9-25 months longer than the life expectancy or survival of female subjects that have low expression of RERG (e.g., below the reference level). Accordingly, the present invention provides for assays and methods to identify mesothelioma subjects that have an improved survival time, and/or good prognosis.

In particular, the inventors have demonstrated herein, by applying a ratio test to the expression profiling data from 39 MPM samples analyzed by Illumina microarray and 48 MPM samples analyzed by Codelink microarray, and 128 samples by microarray, the inventors have identified RERG as a gene differentially expressed in samples that were divided into predicted good and poor outcome groups. In particular, the inventors discovered that RERG was significantly differentially expressed between good and poor outcome samples in both microarrays (p<0.0001). The inventors validated their results on a subset of MPM samples using quantitative real-time PCR (qRT-PCR), and demonstrated that RERG was more highly expressed in good than poor outcome samples (p=0.034). Furthermore, when epithelial MPM microarray samples were divided by RERG expression, there was a significant difference in survival between the three upper quartiles and the lower quartile samples in both microarray platforms (p<0.001). The inventors demonstrated that overexpression of RERG was associated with longer survival or increased overall survival (OS) time of females, e.g., increased the survival of females with mesothelioma by about 9 months or more as compared to females with low expression of RERG (e.g., below a threshold level as disclosed herein). In some embodiments, male mesothelioma subjects who have been identified with levels of RERG expression at or above a reference level (e.g., that overexpress RERG) are identified as suitable subjects to be selected for estrogen therapy as disclosed herein, e.g., with an estrogen or estrogen mimetic.

Accordingly, herein the inventors demonstrate that RERG mediates survival benefit in MPM, and subjects with MPM have increased survival time upon diagnosis of mesothelioma as compared to subjects who do not have high expression of RERG. As RERG is likely activated by estrogen, and women with elevated RERG and mesothelioma have better survival, the inventors have surprisingly discovered that subjects with MPM which have high levels of RERG above a threshold level are amenable and can be treated with estrogen or an estrogen-like molecule, e.g., an estrogen mimetic or molecule which enhances estrogen levels. In some embodiments, the subject is a female subject or with mesothelioma, e.g., MPM. In some embodiments, the subject is a male subject with mesothelioma, e.g., MPM.

According to one aspect, the present invention provides a method of treating or preventing malignant mesothelioma comprising administering to a subject in need therefore an effective amount of a composition comprising estrogen, or an estrogen agent (e.g., agent which elevates estrogen or an estrogen mimetic), where the subject has been identified to have the increased expression of RERG at, or above a pre-defined reference level. In some embodiments, the subject is a female subject. In some embodiments, the subject is a male subject.

In one embodiment, administering a composition comprising an estrogen or estrogen-like agent (e.g., agent which elevates estrogen or an estrogen mimetic) as disclosed herein results in reduction of tumor size. In one embodiment, administering results in reduction of tumor number. In one embodiment, administering prevents an increase in tumor size. In one embodiment, administering a composition comprising an estrogen or estrogen-like agent (e.g., agent which elevates estrogen or an estrogen mimetic) as disclosed herein prevents an increase in tumor number. In one embodiment, administering prevents metastatic progression. In one embodiment, administering a composition comprising an estrogen or estrogen-like agent (e.g., agent which elevates estrogen or an estrogen mimetic) as disclosed herein slows metastatic progression of a mesothelioma which expresses RERG. In one embodiment, administering extends overall survival time of the subject with mesothelioma, particularly a subject that is positive for the biomarker RERG. In one embodiment, administering extends progression-free survival of the subject.

Accordingly, one aspect of the present invention relates to a method of treating a subject with mesothelioma, comprising administering a composition comprising an effective amount of an estrogen or an estrogen mimetic to the subject if a biological sample from the subject has been determined to have an expression of the Ras-like, estrogen-regulated, growth inhibitor (RERG) protein or the RERG gene product at the same level or above a reference level for the RERG protein or gene product. In some embodiments of all aspects of the invention, the method further comprises selecting the subject to be treated before onset of said administering, comprising assaying a biological sample from the subject for the expression of the Ras-like, estrogen-regulated, growth inhibitor (RERG) protein or the RERG gene product, and selecting the subject where the expression of the RERG protein or gene product is at the same level or above a reference level for RERG protein or gene product.

In some embodiments of all aspects of the invention, the mesothelioma is malignant mesothelioma, for example, but not limited to malignant plural mesothelioma (MPM). In some embodiments, the MPM is epithelial MPM.

In some embodiments of all aspects of the invention, the subject is administered an estrogen mimetic which is an estrogen-like agent which has a similar biological function to estrogen. In some embodiments, an estrogen administered to a subject is a natural or synthetic estrogen, such as an estrogen selected from the group consisting of estradiol, estrone, estriol, 17α-estradiol, 17β-estradiol. In some embodiments, an estrogen mimetic administered to a mesothelioma subject is selected from the group consisting of: 2-fluoro-3,17β-estradiol, 2,4-difluoro-3,17β-estradiol, 2-fluoroestrone, 2,4-difluoroestrone, 2-fluoro-17α-ethinyl-3,17β.-estradiol, 2,4-difluoro-17α-ethinyl-3,17β-estradiol, 2-fluoro-17α-ethinylestradiol 3-methyl ether, 2,4-difluoro-17α-ethinylestradiol 3-methyl ether, 15.βH,3'H-cycloprop[14,15]-estra-1,3,5(10),8-tetraen-3,17α-diol, 5.βH,3'H-cycloprop[14,15]-18α-homoestra-1,3,5(10),8-tetraen-3,17α-diol, 17α-hydroxy-15βH,3'H-cycloprop[14,15]-estra-1,3,5(10),8-tetraen-3-yl-pentanoate, 17-methylene-15βH,3'H-cycloprop[14,15]-estra-1,3,5(10),8-tetraen-3-ol, 15βH,3'H-3',3'-difluorocycloprop[14,15]-estra-1,3,5(10),8-tetraen-3,17α-diol, 17-methylene-15βH,3'H-cycloprop[14,15]-estra-1,3,5(10),8-tetraen-3-yl-sulfamate, 17-difluoromethylene-15βH,3'H-cycloprop[14,15]-estra-1,3,5(10),8-tetraen-3-ol, 3-methoxy-15β-methyl-3'H-cycloprop[14,15]-estra-1,3,5(10),8-tetraen-3-ol, 15α-methyl-3'H-cycloprop[14,15]-estra-1,3,5(10),8-tetraen-3,17α-diol, 17-difluoromethylene-15βH,3'H-cycloprop[14,15]-estra-1,3,5(10),8-tetra en-3-yl-(tetramethylenimino)sulfonate and 17-methylene-3'H-cycloprop[8,9]-15.beta.H,3'H-cycloprop[14,15]-estra-1,3,5(10)-trien-3-ol;

In some embodiments, the level of RERG expression is measured in biological sample which comprises a biopsy sample, blood sample, plasma sample, urine sample, and in some embodiments, a biopsy sample is a surgical biopsy, for example, a fine needle aspiration (FNA).

In some embodiments of all aspects of the present invention, a subject to be treated is a female subject. In alternative embodiments, a subject is a male subject. As disclosed herein, the inventors demonstrate that while some male mesothelioma subjects have high RERG expression (e.g., above a reference RERG expression level) they do not have an improved overall survival time (see FIG. 6). Accordingly, the present invention encompasses selecting male mesothelioma subjects with high RERG expression levels and administering an estrogen or estrogen mimetic to improve the prognosis of the male mesothelioma subject and increase the overall survival time after surgery.

In some embodiments, a subject to be treated according to the methods as disclosed herein has had prior exposure to asbestos, and alternatively, in other embodiments, the subject has no known prior exposure to asbestos.

In some embodiments, the method of treating a subject with mesothelioma further comprises administering to the subject an additional therapeutic agent to the subject, prior to, concurrently with, or after administration of an estrogen or estrogen therapy. Such additional therapeutic agents are well known in the art, and include for example but are not limited to, is a chemotherapeutic agent or an agent used to treat mesothelioma, for example, where an agent used to treat mesothelioma can be is selected from the group consisting of pemetrexed, cisplatin and carboplatin or a derivative or analogue thereof. In some embodiments, an additional therapy is tamoxifen or a derivative or analogue thereof.

Another aspect of the present invention relates to an assay comprising: (a) contacting a biological sample from a subject with an affinity binding molecule which binds to the Ras-like, estrogen-regulated, growth inhibitor (RERG) protein or the RERG gene product; (b) measuring the amount of affinity binding molecule which is bound to the RERG protein or RERG gene product; where if a level of the affinity binding molecule which is bound to the RERG protein or RERG gene product is at the same level or above a reference RERG expression level, it indicates that the subject has an increased probability of good prognosis and improved survival time after diagnosis of mesothelioma, whereas if the level of the affinity binding molecule which is bound to the RERG protein is below the reference RERG expression level, it indicates that the subject has an increased probability of a poor prognosis and decreased survival time after diagnosis with mesothelioma.

Another aspect of the present invention relates to an assay comprising: (a) measuring or quantifying the amount of Ras-like, estrogen-regulated, growth inhibitor (RERG) protein or gene expression product in a biological subject obtained from the subject, (b) comparing the measured or quantified amount of RERG protein or gene expression product with a reference value, (c) identifying the subject as having an increased probability of a good prognosis and improved survival time if the amount of RERG protein or gene expression product is the same as, or increased relative to the reference value, and identifying the subject has having an increased probability of a poor prognosis and decreased survival time if the amount of RERG protein or gene expression product is decreased relative to the reference value.

Another aspect of the present invention relates to an assay comprising: (a) contacting a biological sample from a subject with at least one RERG specific antibody or at least one RERG specific probe; wherein the RERG specific antibody or RERG probe comprises a detectable label or means of generating a detectable signal, (b) detecting the presence or intensity of a detectable signal associated with RERG specific antibody or RERG probe; (c) where an increased, or the same level of RERG protein or RERG gene product, (as indicated by the detectable signals), relative to a reference RERG expression level indicates the subject has a probability of a good prognosis and improved survival time after diagnosis of mesothelioma, whereas a decreased level of RERG protein or gene expression product (as indicated by the detectable signals), relative to a reference RERG expression level indicates that the subject has an increased probability of a poor prognosis and decreased survival time after diagnosis with mesothelioma.

Another aspect of the present invention relates to an assay to determine if a subject with mesothelioma will benefit from treatment with an estrogen therapy, the assay comprising: (a) contacting a biological sample obtained from the subject with at least one an affinity binding molecule which binds to the Ras-like, estrogen-regulated, growth inhibitor (RERG) protein or the RERG gene product; (b) measuring the amount of affinity binding molecule which is bound to the RERG protein or RERG gene product, where an increased, or same level of RERG protein or RERG gene product relative to a reference level indicates that the subject will benefit from treatment with estrogen therapy.

In some embodiments of all aspects of the present invention, an assay can comprise an affinity-binding molecule which is a RERG specific antibody or RERG probe, for example, where such the RERG specific antibody or RERG probes can comprise a detectable label or means of generating a detectable signal. In some embodiments, an assay comprises an affinity binding molecule which is attached to a support. In some embodiments, an assay measures the level of RERG gene product by RT-PCR. In some embodiments, an assay can measure the level of RERG protein by measuring the binding of a protein-binding molecule, e.g., but not limited to an antibody or antibody fragment which specifically binds to the RERG protein.

Another aspect of the present invention relates to a computer system for determining if a subject with mesothelioma has a probability of a good prognosis or improved survival time, the system comprising: (a) a measuring module configured to measure the level of the RERG protein and/or RERG gene product in a biological subject obtained from a subject; (b) a storage module configured to store output data from the measuring module; (c) a comparison module adapted to compare the data stored on the storage module with a reference level, and to provide a retrieved content, and (d) a display module for displaying whether the level of RERG protein and/or RERG gene product in a biological sample obtained from a subject is the same as, or greater, by a statistically significant amount, than the reference level and/or displaying the relative levels RERG protein and/or RERG gene product in the biological sample.

In some embodiments, the measuring module measures the presence or intensity of a detectable signal from an affinity-binding molecule which binds to the Ras-like, estrogen-regulated, growth inhibitor (RERG) protein or the RERG gene product, wherein the affinity-binding molecule, comprises a detectable label or means of generating a detectable signal.

In some embodiments of all aspects of the present invention, the measuring module can be configured to detect an affinity-binding molecule which is a protein-binding molecule, such as a RERG specific antibody or the affinity-binding molecule is a protein-binding molecule can be a nucleic-acid binding molecule, such as a RERG probe which can bind to the RERG mRNA, and where, for example, the RERG specific antibody (or antibody fragment) or RERG probes can comprise a detectable label or means of generating a detectable signal. In some embodiments, the measuring module measures the presence or intensity of a detectable signal from an affinity-binding molecule from an immunoassay indicating the level of RERG protein present in the biological sample.

In some embodiments, the level of RERG protein by a protein-binding molecule is measured by immunocytological methods. In some embodiments, the level of RERG gene product is measured by RT-PCR methods.

In some embodiments, a computing module can determine if the level of RERG protein or RERG gene product in the biological sample obtained from a subject is the same as, or greater by a statistically significant amount than the reference level, the display module displays a positive signal indicating that the level in the sample obtained from a subject is greater than that of the reference level. In some embodiments, the computing module can determine if the level of the RERG protein or RERG gene product (e.g., mRNA) is greater by a statistically significant level or alternatively, by at least about 10%, or at least about 20%, or at least about 30% or at least about 50%, or more than 50%, or about 1.5-fold, or at least about 2-fold, or at least about 2.5-fold, or at least about 3-fold or greater than 3-fold than the reference RERG expression level and the display module displays a positive signal that the sample obtained from the subject is greater than the reference value. In some embodiments, a signal indicates that the subject has a good prognosis and/or increased survival time as compared to a subject who has the level of RERG protein or RERG gene product below a reference level. In some embodiments, the reference level is an average REGR expression level in a comparable biological sample (e.g., matched by gender, tissue type etc.) from a population of mesothelioma subjects with a median overall survival time after surgery mesothelioma.

In some embodiments, if the computing module determines that the level of RERG protein or RERG gene product in the biological sample obtained from a subject is below the reference RERG expression level, the display module displays a negative signal indicating that the level in the sample obtained from a subject is lower than that of the reference level. In some embodiments, a can signal indicate that the subject has a poor prognosis and/or decreased survival time as compared to a subject who has the level of RERG protein or RERG gene product at the same level, or above a reference level.

In some embodiments, a signal can indicates that the subject may benefit from treatment with estrogen or an estrogen mimetic, e.g., particularly male mesothelioma subjects who have been determined to have high levels of RERG expression and/or levels of RERG expression (protein and/or mRNA) that are increased by a statistically significant level as compared to a reference level, or are at least about 10%, or at least 20% or more than 20% increased relative to a reference level, or at least about 0.5-fold, or at least about 1.5-fold or at least about 2-fold or greater than a reference RERG expression level.

In some embodiments, a signal can indicate the level of RERG protein or RERG gene product in the biological sample obtained from a subject as compared to the reference level, or a degree of difference of level of RERG protein or RERG gene product as compared to the reference level. In some embodiments, the system as disclosed herein further comprises creating a report based on the level of RERG protein or RERG gene product in the biological sample.

In some embodiments of all aspects of the invention, a biological sample can comprise a biological tissue selected from the group consisting of: whole blood; peripheral blood; whole peripheral blood; biopsy sample, plasma sample; and products thereof.

In some embodiments of all aspects of the invention, the methods, systems and assays as disclosed herein can be used to measure the levels of RERG expression (e.g., protein and mRNA) in a biological sample obtained from a human subject, e.g., a male or female human subject.

According to another aspect, the present invention provides a method for determining if a subject with mesothelioma would likely be responsive to an estrogen therapy, the method comprising: (a) determining the expression level of RERG in a biological sample obtained from the mesothelioma subject, where the expression level of RERG is the mRNA nucleic acid sequence selected from the group consisting of SEQ ID NO: 3 or 4; and (b) comparing the measured RERG mRNA expression level to a reference RERG mRNA expression level, whereby an higher RERG mRNA expression level as compared to the reference level is indicative that the subject will likely be responsive to estrogen therapy. In some embodiments, the method to measure the RERG mRNA levels is by RT-PCT, e.g., quantitative RT-PCT. In some embodiments, the biological sample is obtained from a male subject with mesothelioma.

According to further aspect, the present invention provides a method for determining the prognosis of malignant mesothelioma in a subject comprising; (a) determining the expression level of RERG in a biological sample obtained from the mesothelioma subject, where the expression level of RERG is the mRNA nucleic acid sequence selected from the group consisting of SEQ ID NO: 3 or 4; and (b) comparing the measured RERG mRNA expression level to a reference RERG mRNA expression level, whereby an increase in the RERG expression level (e.g., by a statistically significant amount, or at least about 10%, or at least about 20%, or more than 20%, or at least about 1.5-fold, at least about 2-fold, or at least about 2.5-fold or at least about 3-fold or greater increase) relative to the reference RERG expression level is indicative of good prognosis in said subject (e.g., an increased in overall survival time), and whereas a decreased expression level (as compared to the reference RERG expression) in a subject is indicative of a poor prognosis. In some embodiments, said prognosis is the time to relapse of malignant mesothelioma in said subject. In some embodiments, the reference level is an average REGR expression level in a comparable biological sample (e.g., matched by gender, tissue type and sample type (mRNA or protein) etc.) from a population of mesothelioma subjects with a median overall survival time after surgery mesothelioma.

In some embodiments of the present invention, the subject is a human. In some embodiments, the subject is female and in some embodiments, the subject is male. In some embodiments, the methods of the present invention are used to determine a course of treatment for said subject. For example, a subject identified to have an increased level of RERG as compared to the reference level, the subject is amenable to treatment with an estrogen or estrogen-like agent (e.g., agent which elevates estrogen or an estrogen mimetic) according to the methods as disclosed herein.

In some embodiments, the biological sample obtained from the subject is selected from the group consisting of bodily fluid, a cell line and a tissue sample. In some embodiments the tissue is a fresh, frozen, fixed, wax-embedded or formalin fixed paraffin-embedded (FFPE) tissue. In some embodiments the tissue is mesothelium. In other embodiments the bodily fluid is serum, blood or plasma.

In some embodiments, the expression levels are determined by a method selected from the group consisting of nucleic acid hybridization, nucleic acid amplification, and a combination thereof. In some embodiments, the nucleic acid hybridization is performed using a solid-phase nucleic acid biochip array or in situ hybridization. In one embodiment, the nucleic acid amplification method is real-time PCR. In some embodiment, the RT-PCR method comprises forward and reverse primers.

Another aspect of the present invention also provides a kit for determining a prognosis of a subject with mesothelioma, said kit comprising an affinity binding molecule that can bind to the RERG protein and/or RERG gene product. In some embodiments, the kit comprises reagents for performing in situ hybridization analysis or RT-PCR.

DETAILED DESCRIPTION OF THE INVENTION

Figure 1:
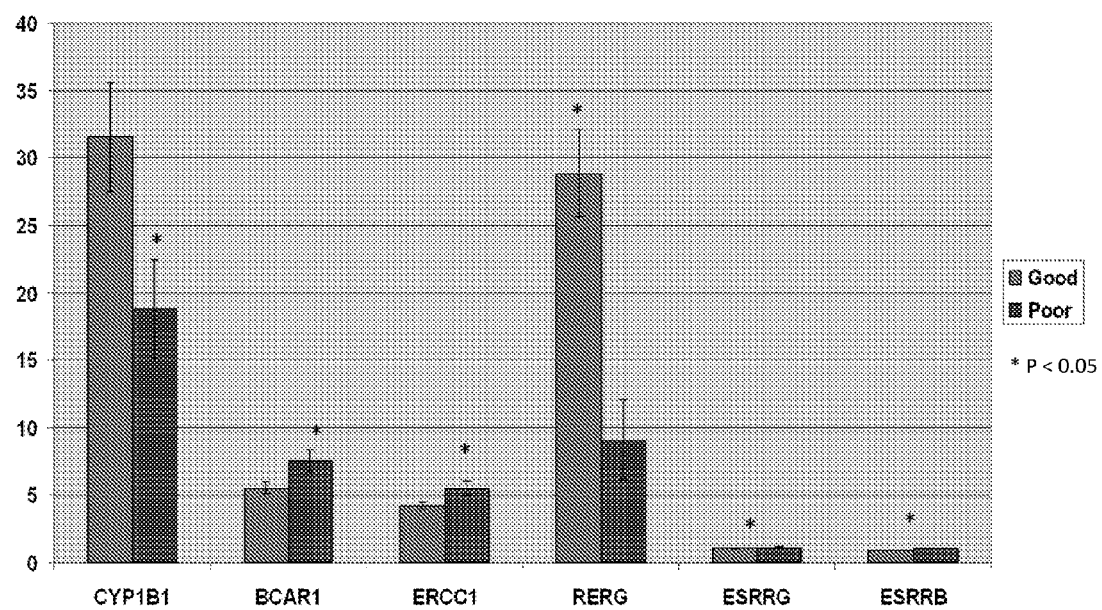
FIG. 1 is a histogram of the differentially expressed candidate estrogen-regulated genes in 40 samples assessed by illumina array showing that RERG is differentially expressed in samples from mesothelioma subjects predicted to have a good prognosis or bad prognosis. RERG was demonstrated to be at least about 2-fold greater in samples from mesothelioma subjects predicted to have a good outcome as compared to mesothelioma subjects predicted to have a poor outcome.

Described herein are methods for treatment of mesothelioma, and methods, assays, and systems relating to determining the prognosis of a subject with mesothelioma, and for predicting the therapeutic responsiveness of a subject treated with estrogen or an estrogen elevating compound, as disclosed herein. The assays and methods described herein rely upon the inventors' demonstration of a clinically meaningfully assay directed to determining the level of the RERG biomarker in a biological sample from the subject, and the correlation of the results of such assays to determine if a subject is amenable to treatment with estrogen or an estrogen-like compound (e.g., an agent which elevates or is a mimetic of estrogen), as well as prognosis outcome in survival with mesothelioma.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in U.S. Pat. Nos. 4,965,343, and 5,849,954; Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.); which are all incorporated by reference herein in their entireties.

The term "RAS-like, estrogen-regulated, growth inhibitor" is referred to herein as "RERG" and is also known as aliases: RAS-like, estrogen-regulated, growth inhibitor 1, MGC157541, ras-related and estrogen-regulated growth inhibitor 2. The human mRNA is encoded by Ref Seq ID No: NM_032918.2 (variant 1) (SEQ ID NO: 1) and NM_001190726.1 (isoform 2) (SEQ ID NO: 2), which encode for proteins in two alternative isoforms: NP_116307.1 (SEQ ID NO: 3) and NP_001177655.1 (SEQ ID NO: 4) respectively.

The terms "decrease," "reduce," "reduced", and "reduction" are all used herein generally to mean a decrease by a statistically significant amount relative to a reference. However, for avoidance of doubt, "reduce," "reduction", or "decrease" typically means a decrease by at least 10% as compared to the absence of a given treatment and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the absence of a given treatment, or any decrease between 10-99% as compared to the absence of a given treatment.

The terms "increased", "increase", or "enhance" are all used herein to generally mean an increase by a statically significant amount; for the avoidance of any doubt, the terms "increased", "increase", or "enhance" means an increase of at least 10% as compared to a reference level, for example an increase can be at least about 10% or at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein in the context of expression, the terms "treat," "treatment," and the like, as used in the context of the therapeutic methods described herein, refer to a decrease in severity, indicators, symptoms, and/or markers of mesothelioma as described herein. In the context of the present invention insofar as it relates to any of the conditions recited herein, the terms "treat," "treatment," and the like mean to relieve, alleviate, ameliorate, inhibit, slow down, reverse, or stop the progression, aggravation, deterioration, anticipated progression or severity of at least one symptom or complication associated with mesothelioma. In one embodiment, a symptom of mesothelioma is alleviated by at least 10%, at least 20%, at least 30%, at least 40%, or at least 50% or more than 50%.

As used herein, the term "administer" refers to the placement of a composition into a subject by a method or route which results in delivery of at least part of the administered composition to a desired site such that the desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, topical (including buccal and sublingual), intracranial, and intracerebral administration. Administering includes, but is not limited to, administering by a medical professional and self-administering. "Pulmonary administration" means administration or delivery to the pulmonary epithelium or endothelium. Pulmonary delivery methods include, but are not limited to, aerosols, metered dose inhaler systems, powders (dry powder inhalers) and solutions (nebulizers), which may contain nanostructures such as micelles, liposomes, nanoparticles, and microemulsion delivery by aerosol and bronchoscopic instillation. "Parenteral administration" means administration through injection or infusion. Parenteral administration includes, but is not limited to, subcutaneous administration, intravenous administration, or intramuscular administration. "Subcutaneous administration" means administration just below the skin. "Intravenous administration" means administration into a vein. "Intratumoral administration" means administration within a tumor. "Chemoembolization" means a procedure in which the blood supply to a tumor is blocked surgically or mechanically and chemotherapeutic agents are administered directly into the tumor. "Intracavitary administration" means administration directly into a cavity with suspected or diagnosed tumor with said cavity represented as either left or right pleural cavity or the abdominal cavity or the pericardial space.

The term "amelioration" as used herein, refers to a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

In some embodiments, a "subject" as used herein can be a male human or male animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf. Patient or subject includes any subset of the foregoing, e.g., all of the above. In certain embodiments, the subject is a mammal, e.g., a primate, e.g., a human.

Preferably, the subject is a mammal. The mammal can be a human, non-human primate, mouse, rat, dog, cat, horse, or cow, but is not limited to these examples. Mammals other than humans can be advantageously used as subjects that represent animal models of mesothelioma. In addition, the methods and assays described herein can be used to treat domesticated animals and/or pets. A subject can be one who has been previously diagnosed with or identified as suffering from or having prostate cancer or one or more complications related to prostate cancer, and optionally, but need not have already undergone treatment for mesothelioma or the one or more complications related to mesothelioma. Alternatively, a subject can also be one who has not been previously diagnosed as having mesothelioma or one or more complications related to mesothelioma. For example, a subject can be one who exhibits one or more risk factors for mesothelioma or one or more complications related to mesothelioma or a subject who does not exhibit mesothelioma risk factors.

The term "biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum stool, tears, mucus, hair, and skin. Biological samples also include explants and primary and/or transformed cell cultures derived from animal or patient tissues.

Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, cellular content of fine needle aspiration (FNA) or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

As used herein, "mesothelioma" refers to a cancer affecting the membrane linings of the lungs and abdomen. Mesothelioma is an aggressive form of cancer, and includes malignant mesothelioma. The term "mesothelioma" as used herein includes; Pleural mesothelioma (MPM) (affecting the lung's protective lining in the chest cavity, which represents about three quarters of all mesothelioma incidence), Peritoneal mesothelioma (which affects the abdominal cavity and pericardial mesothelioma, which affects the cardiac cavity), and Testicular mesothelioma (which is typically extremely rare and typically presents with metastases of the peritoneal variety). Encompassed in the term mesothelioma are mesotheliomas of the three recognized mesothelioma cell-types; epithelial cell-type mesothelioma (which comprises between 50 and 70% of all mesotheliomas), sarcomatoid mesothelioma and biphasic mesothelioma. Symptoms of mesothelioma include, but are not limited to In one embodiment, the subject has exhibited at least one symptom selected from the group anemia, blood clotting disorder, bowel obstruction, chest pain, persistent dry or raspy cough, coughing up blood (hemoptysis), shortness of breath (dyspnea), pain in the lower back or rib area, painful breathing, development of lumps under the skin on the chest, difficulty with swallowing (dysphagia), night sweats or fever, nausea, unexplained weight loss, fatigue, abdomen, pericardium, peritoneal and/or pleural effusion.

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: mesothelioma, glioblastoma, apudoma, choristoma, branchioma, malignant carcinoid syndrome, carcinoid heart disease, carcinoma (e.g., Walker, basal cell, basosquamous, Brown-Pearce, ductal, Ehrlich tumor, small cell lung, non-small cell lung (e.g., lung squamous cell carcinoma, lung adenocarcinoma and lung undifferentiated large cell carcinoma), oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myo sarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

The term "estrogen" is also known as estrogens (AmE), or oestrogen (BE), refer to a group of compounds important in the estrous cycle of humans and other animals. The term "estrogen" includes the three major naturally occurring estrogens in women; estrone (E1), estradiol (E2), and estriol (E3), which are well known in the art. Estradiol is the predominant estrogen during reproductive years both in terms of absolute serum levels as well as in terms of estrogenic activity. All of the different forms of estrogen are synthesized from androgens, specifically testosterone and androstenedione, by the enzyme aromatase. Estrogen can be administered in skin patches, e.g., estradiol skin patches such as ESTRADERM™.

The term "estrogen-like agent" as used herein refers to an estrogen mimetic or molecule or agent which increases estrogen or elevates estrogen levels in a cell. For example, an estrogen-like agent includes premarin, a commonly prescribed estrogenic drug produced from the urine of pregnant mares, contains the steroidal estrogens equilin and equilenin.

The term "estrogen mimetic" as disclosed herein refers to compounds which possess a biological activity (in particular functional biological activity) that is substantially similar in biological activity to estrogen. An estrogen mimetic includes a range of synthetic and natural substances have been identified that also possess estrogenic activity, for example, synthetic substances known as xenoestrogens, plant products with estrogenic activity called phytoestrogens, and fungal products with estrogenic activity known as mycoestrogens.

The term "mimetic" can also be known as a "functional derivative" and can be used interchangeably herein, and refer to compounds which possess a biological activity (in particular functional biological activity) that is substantially similar to the biological activity of the entity or molecule for which it's a functional derivative of. The term functional derivative is intended to include the fragments, variants, analogues or chemical derivatives of a molecule. In certain embodiments, functional derivatives and functional analogues of estrogen can be assessed for their biological activity by one of ordinary skill in the art using commonly known methods, where derivatives and analogues which activate the estrogen receptor (ER) would be considered as functional derivatives or functional analogues of estrogen.

The term "analog" as used herein refers to an agent that retains the same, or a substantially similar biological function (i.e., binding to a receptor, such as the estrogen receptor) and/or structure as the molecule or chemical or polypeptide it is an analogue of. Examples of analogs include peptidomimetics (a peptide analog), peptide nucleic acids (a nucleic acid analog), small and large organic or inorganic compounds, as well as derivatives and variants of a polypeptide or nucleic acid herein.

The term "substantially similar", when used to define the biological activity of a mimetic of estrogen as compared to the biological activity of estrogen to which it is a mimetic of, means that a particular mimetic differs from the initial hormone estrogen (17β-estradiol) in chemical structure, by one or more groups or elements, including substitutions, deletions, or additions of groups of elements, the net effect of which is to retain at least some of the biological activity found in the initial estrogen with respect to the biological activity of estrogen with respect to activation of the ER receptor or estrogen G protein-coupled receptor GPR30 (GPER). Such biological activity can be assessed by one of ordinary skill in the art using an assay well known in the art. As such, estrogen mimetics having lesser degrees of structural similarity but a substantially similar or comparable biological activity of the original hormone estrogen (17β-estradiol) from which it is based with respect to activation of the ER receptor or GPR30 receptor are considered to be equivalents. Substantially similar derivatives or analogues of estrogen (17β-estradiol) will typically have at least about 60%, or at least about 70% or at least about 80% or at least about 90% or at least about 95%, or at least about 100% the biological activity of ER or GPR30 activation as compared to the estrogen (17β-estradiol) it is a mimetic of, or at least at least 2-fold, or at least about 3-fold, or at least about a 4-fold, or at least about a 5-fold or at least about a 10-fold, or any increase between 2-fold and 10-fold or greater the biological activity of ER or GPR30 activation as compared to estrogen (17β-estradiol) are to be considered a mimetic of estrogen (17β-estradiol) they are based on.

The term "xenoestrogens" are a type of xenohormone that imitates estrogen and can be either synthetic or natural chemical compounds. Synthetic xenoestrogens include, without limitation, industrial compounds, such as PCBs, BPA and phthalates, which have estrogenic effects on a living organism even though they differ chemically from the estrogenic substances produced internally by the endocrine system of any organism. Natural xenoestrogens include phytoestrogens which are plant-derived xenoestrogens. Because the primary route of exposure to these compounds is by consumption of phytoestrogenic plants, they are sometimes called "dietary estrogens". Mycoestrogens, estrogenic substances from fungi, are another type of xenoestrogen that are also considered mycotoxins. Xenoestrogens include pharmacological estrogens (estrogenic action is an intended effect, as in the drug ethinyl estradiol used in contraceptive pill), but other chemicals may also have estrogenic effects. Xenoestrogens have been introduced into the environment by industrial, agricultural and chemical companies and consumers only in the last 70 years or so, but archiestrogens have been a ubiquitous part of the environment even before the existence of the human race given that some plants (like the cereals and the legumes) are using estrogenic substances possibly as part of their natural defense against herbivore animals by controlling their male fertility.

The term "phytoestrogens" are plant-derived xenoestrogens functioning as the primary female sex hormone (see estrogen) not generated within the endocrine system but consumed by eating phytoestrogenic plants. Also called "dietary estrogens", they are a diverse group of naturally occurring nonsteroidal plant compounds that, because of their structural similarity with estradiol (17-β-estradiol), have the ability to cause estrogenic or/and antiestrogenic effects. Phytoestrogens exert their effects primarily through binding to estrogen receptors (ER). There are two variants of the estrogen receptor, alpha (ER-α) and beta (ER-β) and many phytoestrogens display somewhat higher affinity for ER-β compared to ER-α. Phytoestrogens mainly belong to a large group of substituted natural phenolic compounds: the coumestans, prenylated flavonoids and isoflavones are three of the most active in estrogenic effects in this class. The key structural elements that enable phytoestrogens to bind with high affinity to estrogen receptors and display estradiol-like effects are: The phenolic ring that is indispensable for binding to estrogen receptor, the ring of isoflavones mimicking a ring of estrogens at the receptors binding site, low molecular weight similar to estrogens (MW=272), distance between two hydroxyl groups at the isoflavones nucleus similar to that occurring in estradiol, optimal hydroxylation pattern.

The term "mycoestrogens" are estrogens produced by fungi. The most important mycoestrogen is zearalenone, produced by Fusarium species of fungi.

The term "chemotherapeutic agent" as used herein is a drug used to treat a disease, especially cancer. In relation to cancer the drugs typically target rapidly dividing cells, such as cancer cells. Non-limiting examples of chemotherapeutic agents include cisplatin, carboplatin, camptothecins, doxorubicin, cyclophosphamide, paclitaxel, etoposide, vinblastine, Actinomycin D and cloposide.

As used herein, the term "classification" refers to a procedure and/or algorithm in which individual items are placed into groups or classes based on quantitative information on one or more characteristics inherent in the items (referred to as traits, variables, characters, features, etc) and based on a statistical model and/or a training set of previously labeled items. According to one embodiment, classification means determination of the type of cancer. In one embodiment, classification determines a type of classification of poor or good prognosis or improved survival time or decreased survival time after diagnosis with mesothelioma.

The term "detection" as used herein means detecting the presence of a component in a sample. Detection also means detecting the absence of a component. Detection also means measuring the level of a component, either quantitatively or qualitatively. Detection also means identifying or diagnosing cancer in a subject. "Early detection" means identifying or diagnosing cancer in a subject at an early stage of the disease, especially before it causes symptoms.

The term "gene" as used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated or regulatory sequences linked thereto.

The term "gene product" as used herein refers to include RNA transcribed from a gene, or a polypeptide encoded by a gene or translated from RNA. In some embodiments, the term gene product refers to mRNA transcribed from the gene.

The term "identical" or "identity" as used herein in the context of two or more nucleic acids or polypeptide sequences mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

The term "In Situ Detection" as used herein means the detection of expression or expression levels in the original site hereby meaning in a tissue sample such as biopsy.

The term "metastasis" as used herein means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

The term "modulation" as used herein means a perturbation of function or activity. In certain embodiments, modulation means an increase in gene expression. In certain embodiments, modulation means a decrease in gene expression.

The term "nucleic acid" or "oligonucleotide" or "polynucleotide", as used herein, mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single-stranded or double-stranded, or may contain portions of both double-stranded and single-stranded sequence. The nucleic acid may be DNA, both genomic and cDNA, RNA, or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e., ribonucleotides, containing a non-naturally occurring nucleobase instead of a naturally occurring nucleobase such as uridines or cytidines modified at the 5-position, e.g., 5-(2-amino)propyl uridine, 5-bromo uridine; adenosines and guanosines modified at the 8-position, e.g., 8-bromo guanosine; deaza nucleotides, e.g., 7-deaza-adenosine; O- and N-alkylated nucleotides, e.g., N6-methyl adenosine are suitable. The 2'-OH-group may be replaced by a group selected from H, OR, R, halo, SH, SR, $NH_2$, MIR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al. (Nature 438:685-689 (2005)) and Soutschek et al. (Nature 432:173-178 (2004)), which are incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver. Mixtures of naturally occurring nucleic acids and analogs may be made; alternatively, mixtures of different nucleic acid analogs, and mixtures of naturally occurring nucleic acids and analogs may be made.

The term "affinity-binding molecule" is used herein to refer to an agent which binds to a second agent, e.g., a protein or nucleic acid, with specific affinity, as that term is defined herein. An affinity-binding molecule can be a protein binding molecule (e.g., an affinity binding molecule which binds with specific affinity to the protein of interest) or a nucleic-acid binding molecule (e.g., an affinity binding molecule which binds with specific affinity to a nucleic acid of interest.)

The term "protein binding moiety" is used interchangeably herein with "protein binding molecule" or protein binding entity" and refers to any entity which has specific affinity for a protein. The term "protein-binding molecule" also includes antibody-based binding moieties and antibodies and includes immunoglobulin molecules and immunologically active determinants of immunoglobulin molecules, e.g., molecules that contain an antigen binding site which specifically binds (immunoreacts with) to the RERG protein. The term "antibody-based binding moiety" is intended to include whole antibodies, e.g., of any isotype (IgG, IgA, IgM, IgE, etc), and includes fragments thereof which are also specifically reactive with the Psap proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-based binding moiety" includes polyclonal, monoclonal, or other purified preparations of antibodies and recombinant antibodies. The term "antibody-based binding moiety" is further intended to include humanized antibodies, bispecific antibodies, and chimeric molecules having at least one antigen binding determinant derived from an antibody molecule. In a preferred embodiment, the antibody-based binding moiety detectably labeled. In some embodiments, a "protein-binding molecule" is a co-factor or binding protein that interacts with the protein to be measured, for example a co-factor or binding protein to RERG protein.

The term "labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of Psap or Tsp-1 present in the tissue samples correlate to the intensity of the signal emitted from the detectably labeled antibody.

The term "specific affinity" or "specifically binds" or "specific binding" are used interchangeably herein refers to an entity such as an affinity-binding molecule, e.g., a protein-binding molecule or nucleic-acid binding molecule, that recognizes and binds a desired polypeptide or nucleic acid respectively, but that does not substantially recognize and bind other molecules in a sample, for example, a biological sample.

The term "antibody" is meant to be an immunoglobulin protein that is capable of binding an antigen. Antibody as used herein is meant to include antibody fragments, e.g. $F(ab')_2$, Fab', Fab, capable of binding the antigen or antigenic fragment of interest.

The term "humanized antibody" is used herein to describe complete antibody molecules, i.e. composed of two complete light chains and two complete heavy chains, as well as antibodies consisting only of antibody fragments, e.g. Fab, Fab', $F(ab')_2$, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions of the antibody molecule are derived from a nucleic acid sequence encoding a human antibody. Such human antibodies are most desirable for use in antibody therapies, as such antibodies would elicit little or no immune response in the human subject.

The term "chimeric antibody" is used herein to describe an antibody molecule as well as antibody fragments, as described above in the definition of the term "humanized antibody." The term "chimeric antibody" encompasses humanized antibodies. Chimeric antibodies have at least one portion of a heavy or light chain amino acid sequence derived from a first mammalian species and another portion of the heavy or light chain amino acid sequence derived from a second, different mammalian species. In some embodiments, a variable region is derived from a non-human mammalian species and the constant region is derived from a human species. Specifically, the chimeric antibody is preferably produced from a 9 nucleotide sequence from a non-human mammal encoding a variable region and a nucleotide sequence from a human encoding a constant region of an antibody.

In the context of this invention, the term "probe" refers to a molecule which can detectably distinguish between target molecules differing in structure. Detection can be accomplished in a variety of different ways depending on the type of probe used and the type of target molecule, thus, for example, detection may be based on discrimination of activity levels of the target molecule, but preferably is based on detection of specific binding. Examples of such specific binding include antibody binding and nucleic acid probe hybridization. Thus, for example, probes can include enzyme substrates, antibodies and antibody fragments, and preferably nucleic acid hybridization probes.

The term "label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

As used herein the term "reference level" when used in the context of the reference level of RERG refers to the level of RERG protein or RERG gene product (e.g., mRNA) in at least one reference biological sample, or a group of biological samples from at least one subject or a group of subjects which have been identified to be healthy or not have mesothelioma. By way of example, a positive reference level is a level of the level of RERG expression (e.g. protein or mRNA) which is at or above a reference value (e.g., reference RERG expression level) and indicates the subject is predicted to have a good prognosis and/or improved overall survival time as compared to a subject who has a RERG expression below a reference RERG expression level. A negative reference level is a level of RERG expression which indicates the subject is predicted to have a poor prognosis and/or decreased overall survival after surgery from mesothelioma. In some embodiments, a positive reference level is normalized to 100%, where 100% represents a high level of RERG expression, and in some embodiments a negative reference level is normalized to 0%, where 0% represents a low RERG expression. Thus, so an increase in the level of RERG expression, such as an increase of at least 1% to 100% of the level of RERG expression in a biological sample as compared with a negative reference level, including all percentages between 1% and 100%, i.e. at least 1%, 2%, 3%, 4%, 5%, 10%, 15%, 20%, 25%, 30%, 35%, 40%, 45%, 50%, 60%, 70%, 80%, 90%, 95%, 100% indicates the degree of likelihood (i.e. %) that the subject whom the biological sample has been obtained from is likely to have a good prognosis and increased overall survival time. Stated another way, if the level of RERG expression is 30% higher than reference RERG expression level, then the subject is likely to have an increased survival time as compared to a subject who does not have a higher RERG expression level than the reference level. In some embodiments, the reference level is an average REGR expression level in a comparable biological sample (e.g., matched by gender, tissue type etc.) from a population of mesothelioma subjects with a median overall survival time after surgery mesothelioma.

The term "support" refers to conventional supports such as beads, particles, dipsticks, fibers, filters, membranes and silane or silicate supports such as glass slides.

The term "overall survival time" or "survival time", as used herein means the time period for which a subject survives after diagnosis of or treatment for a disease. In certain embodiments, the disease is mesothelioma, and in some embodiments, the disease is malignant mesothelioma (MM), and in some embodiments the disease is malignant plural mesothelioma (MPM).

The term "pharmaceutical agent" as used herein means a substance that provides a therapeutic effect when administered to a subject. "Pharmaceutical composition" means a mixture of substances suitable for administering to an individual that includes a pharmaceutical agent. For example, a pharmaceutical composition may comprise an estrogen or estrogen mimetic and a sterile aqueous solution. "Active pharmaceutical ingredient" means the substance in a pharmaceutical composition that provides a desired effect.

The term "prevention" as used herein means delaying or forestalling the onset or development or progression of a condition or disease for a period of time, including weeks, months, or years.

The term "progression-free survival" means the time period for which a subject having a disease survives, without the disease getting worse. In certain embodiments, progression-free survival is assessed by staging or scoring the disease. In certain embodiments, progression-free survival of a subject having mesothelioma is assessed by evaluating tumor size, tumor number, and/or metastasis or number of metastasis.

The term "probe" as used herein means an oligonucleotide or nucleic acid or analogue capable of binding to a target nucleic acid (e.g., the RERG mRNA) of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

The term "reduced tumorigenicity" as used herein refers to the conversion of hyperproliferative (e.g., neoplastic)

cells to a less proliferative state. In the case of tumor cells, "reduced tumorigenicity" is intended to mean tumor cells that have become less tumorigenic or non-tumorigenic or non-tumor cells whose ability to convert into tumor cells is reduced or eliminated. Cells with reduced tumorigenicity either form no tumors in vivo or have an extended lag time of weeks to months before the appearance of in vivo tumor growth. Cells with reduced tumorigenicity may also result in slower growing three dimensional tumor mass compared to the same type of cells having fully inactivated or non-functional tumor suppressor gene growing in the same physiological milieu (e.g., tissue, organism age, organism sex, time in menstrual cycle, etc.).

As used herein the term "reference expression profile" means a value that statistically correlates to a particular outcome when compared to an assay result. In preferred embodiments the reference value is determined from statistical analysis of studies that compare the RERG expression level with known clinical outcomes, e.g., poor and good outcome classification groups. The reference value may be a threshold score value or a cutoff score value. Typically a reference value will be a threshold above which one outcome is more probable and below which an alternative threshold is more probable. For example, if the level of RERG expression measured from a subject is above, of the same value as a reference value for RERG expression, then the outcome is more probable to be a good outcome, and increased overall survival time. Conversely, if the RERG level measured from the subject is below the reference value, the outcome for the subject is more probable to be a poor outcome, with decreased survival time as compared to a subject who has the RERG expression at or above the threshold value.

The term "stringent hybridization conditions" as used herein mean conditions under which a first nucleic acid sequence (e.g., probe) will hybridize to a second nucleic acid sequence (e.g., target, e.g., RERG mRNA), such as in a complex mixture of nucleic acids. Stringent conditions are sequence-dependent and will be different in different circumstances. Stringent conditions may be selected to be about 5-10° C. lower than the thermal melting point ($T^m$) for the specific sequence at a defined ionic strength pH. The $T^m$ may be the temperature (under defined ionic strength, pH, and nucleic acid concentration) at which 50% of the probes complementary to the target hybridize to the target sequence at equilibrium (as the target sequences are present in excess, at $T^m$, 50% of the probes are occupied at equilibrium).

Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

The term "therapy" as used herein means a disease treatment method. In certain embodiments, therapy includes, but is not limited to, estrogen therapy (e.g., administration of an estrogen or mimetic thereof), alone or in combination with other cancer treatments, e.g., but not limited to chemotherapy, surgical resection, transplant, radiation therapy, "gene therapy", immunotherapy, and/or chemoembolization. The term "therapeutic agent" means a pharmaceutical agent used for the cure, amelioration or prevention of a disease. "Recommended therapy" means a treatment recommended by a medical professional for the treatment, amelioration, or prevention of a disease.

The term "effective amount" as used herein refers to the amount of an estrogen or estrogen mimetic needed to alleviate at least one or more symptom of the disease or disorder, and relates to a sufficient amount of a composition to provide the desired effect. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease or in some embodiments, increasing overall survival time as compared to a subject who has not been administered an estrogen or estrogen mimetic. The specific "effective amount" will, obviously, vary with such factors as the particular condition being treated, the physical condition of the subject, the type of subject being treated, the duration of the treatment, the route of administration, the type of estrogen or estrogen mimetic being used, the nature of concurrent therapy (if any), and the specific formulations employed, the structure of each of these components or their derivatives. Thus, it is not generally practicable to specify an exact "effective amount". However, for any given case, an appropriate "effective amount" can be determined by one of ordinary skill in the art using only routine experimentation.

The term "therapeutically effective amount" therefore refers to an amount or dose of an estrogen or estrogen mimetic that is sufficient to effect a particular effect when administered to a typical subject. In some instances, the term "therapeutically effective amount" or "therapeutically efficient", refers to a dosage of estrogen or mimetic thereof, that provides the specific pharmacological response for which the estrogen or estrogen mimetic is administered in a significant number of subjects in need of such treatment. The "therapeutically effective amount" may vary according to, for example, the physical condition of the patient, the age of the patient and the severity of the disease.

As used herein, a "pharmaceutical carrier" is a pharmaceutically acceptable solvent, suspending agent or vehicle for delivering an estrogen or estrogen mimetic to the subject. The carrier may be liquid or solid and is selected with the planned manner of administration in mind. Each carrier must be pharmaceutically "acceptable" in the sense of being compatible with other ingredients of the composition and non injurious to the subject.

As used herein, the phrase "threshold expression level" refers to a reference expression value or RERG expression. Measured values (e.g., from a biological sample obtained from the subject) are compared to a corresponding threshold expression level to determine the prognosis of a subject with mesothelioma.

As used herein, the term "a tissue sample" is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

The term "Unit dosage form", used herein, may refer to a physically discrete unit suitable as a unitary dosage for a human or animal subject. Each unit may contain a predetermined quantity of a composition described herein, calculated in an amount sufficient to produce a desired effect in association with a pharmaceutically acceptable diluent, carrier or vehicle. The specifications for a unit dosage form may depend on the particular composition employed and the effect to be achieved, and the pharmacodynamics associated with the composition in the host.

The term "statistically significant" or "significantly" refers to statistical significance and generally means a two standard deviation (2SD) difference as compared to a reference level, e.g., a reference concentration of REGR expression. The term refers to statistical evidence that there is a difference. It is defined as the probability of making a decision to reject the null hypothesis when the null hypothesis is actually true. The decision is often made using the p-value.

Other than in the operating examples, or where otherwise indicated, all numbers expressing quantities of ingredients or reaction conditions used herein should be understood as modified in all instances by the term "about." The term "about" when used in connection with percentages can mean±1%.

Other terms are defined herein within the description of the various aspects of the invention.

In some embodiments, the methods, systems, and assays described herein relate to determining if a subject with mesothelioma is suitable for treatment with estrogen or an estrogen-like agent (e.g., an agent which increases estrogen and/or estrogen mimetic), as well as the methods, systems, and assays as a prognostic indicator of the survival of a subject with mesothelioma.

Treatment of Mesothelioma

One aspect of the present invention is a method of treating a subject with mesothelioma, for example, where the subject is identified to have an expression level of RERG at, or above a reference value for RERG expression. For example, where the RERG protein level and/or RERG expression level (e.g., RERG gene product, e.g., mRNA level) is at or above a reference level for the RERG protein level and/or RERG expression level, the subject is amenable to treatment with an estrogen or an estrogen mimetic or an estrogen-like molecule.

In one embodiment, the present invention provides a method of treating a subject with mesothelioma, comprising administering a composition comprising an effective amount of an estrogen or an estrogen mimetic to the subject if a biological sample from the subject has been determined to have an expression of the Ras-like, estrogen-regulated, growth inhibitor (RERG) protein or the RERG gene product at the same level or above a reference level for the RERG protein or gene product.

In some embodiments, a subject can be diagnosed with mesothelioma after the administration of medical tests well-known to those in the medical profession. In certain embodiments, the present invention provides methods for the treatment of mesothelioma comprising administering to a subject in need thereof a pharmaceutical composition comprising one or more estrogens or estrogen mimetic. Administration of a pharmaceutical composition of the present invention to a subject having mesothelioma may result in one or more clinically desirable outcomes. Such clinically desirable outcomes include reduction of tumor number or reduction of tumor size. Additional clinically desirable outcomes include the extension of overall survival time of the subject, and/or extension of progression-free survival time of the subject. In certain embodiments, administration of a pharmaceutical composition of the invention prevents an increase in tumor size and/or tumor number. In certain embodiments, administration of a pharmaceutical composition of the invention prevents the recurrence of tumors. Administration of a pharmaceutical composition of the present invention results in desirable phenotypic effects. A subject's response to treatment may be evaluated by tests similar to those used to diagnosis the mesothelioma. Response to treatment may also be assessed by measuring biomarkers in blood, for comparison to pre-treatment levels of biomarkers.

The compounds provided herein useful for the treatment of mesothelioma include estrogens, such as, but not limited to estrone (E1), estradiol (E2), and estriol (E3), as well as xenoestrogens, phytoestrogens and mycoestrogens. In some embodiments, a subject identified to have increased expression of RERG as disclosed herein is administered a composition comprising estrogen or an estrogen-like agent (e.g., an agent which elevates estrogen or an estrogen mimetic). Such a compound is well known in the art, for example is disclosed in U.S. Pat. Nos. 4,605,649, 6,245,756, which are incorporated herein in their entirety by reference.

The use of natural and synthetic estrogens with systematic action, i.e. in all organs and systems of the body area encompassed for use in the methods and systems of the present invention. In some embodiments, natural and synthetic estrogens encompassed for use in the methods as disclosed herein are disclosed in the following patents: U.S. Pat. No. 4,897,389, U.S. Pat. No. 5,554,601, International Patent Documents WO 95/12402 and WO 97/03661 and German Patent Document DE 43 38 314 C1, which are incorporated herein by reference in their entireties.

U.S. Pat. No. 4,897,389 protects the use of estradiol, estrone and estriol, alone or in combination with gonadotropins, androgens, anabolic androgens or human growth hormones, for treatment of senile dementia, Morbus Parkinsons, cerebral atrophy, Morbus Alzheimers, cerebellar atrophy, senile or essential tremor. U.S. Pat. No. 5,554,601 and WO 95/12402 protects the use of estrogen substances which have slight "sexual activity" for protection of nerve cells from progressive damage and cell death, and for treatment of neurodegenerative diseases. The estrogen, 17.alpha.-estradiol, is mentioned as an example of a substance with slight "sexual activity" and neuroprotective action.

WO 97/03661 protects the use of non-estrogenic substances, which have at least two ring structures, in which at least one is a terminal phenolic ring, and whose molecular weight is less than 1000 Daltons, to guarantee neuroprotection.

German Patent Document DE 43 38 314 C1 describes steroids with a phenolic A ring structure, whose radical trapping and antioxidative properties, do not depend on the extent of their estrogen-similar activity. These compounds can be used for prophylaxis and therapy of radical-mediated cell damage.

Additional estrogen-like agents, or compounds falling within the scope of the estrogen-like compounds, or estrogen mimetics include, but are not limited to 2-fluoro-3,17β-estradiol, 2,4-difluoro-3,17β-estradiol, 2-fluoroestrone, 2,4-difluoroestrone, 2-fluoro-17α-ethinyl-3,17β.-estradiol, 2,4-difluoro-17α-ethinyl-3,17β-estradiol, 2-fluoro-17α-ethinylestradiol 3-methyl ether, 2,4-difluoro-17α-ethinylestradiol 3-methyl ether, 15.βH,3'H-cycloprop[14,15]-estra-1,3,5(10),8-tetraen-3,17α-diol, 5.βH,3'H-cycloprop[14,15]-18α-homoestra-1,3,5(10),8-tetraen-3,17α-diol, 17α-hydroxy-15βH,3'H-cycloprop[14,15]-estra-1,3,5(10),8-tetraen-3-yl-pentanoate, 17-methylene-15βH, 3'H-cycloprop[14,15]-estra-1,3,5(10),8-tetraen-3-ol, 15βH, 3'H-3',3'-difluorocycloprop[14,15]-estra-1,3,5(10),8-tetraen-3,17α-diol, 17-methylene-15βH,3'H-cycloprop[14,15]-estra-1,3,5(10),8-tetraen-3-yl-sulfamate, 17-difluoromethylene-15βH,3'H-cycloprop[14,15]-estra-1,3,5(10),8-tetra en-3-ol, 3-methoxy-15β-methyl-3'H-cycloprop[14,15]-estra-1,3,5(10),8-tetraen-3-ol, 15α-methyl-3'H-cycloprop[14,15]-estra-1,3,5(10),8-tetraen-3,17α-diol, 17-difluoromethylene-15βH,3'H-cycloprop[14,15]-estra-1,3,5(10),8-tetra en-3-yl-(tetramethylenimino)sulfonate and 17-methylene-3'H-cycloprop[8,9]-15.beta.H,3'H-cycloprop[14,15]-estra-1,3,5(10)-trien-3-ol; 17-methylene-3'H-cycloprop[8,9]-15.beta.H,3'H-cycloprop[14,15]-estra-1,3,5(10)-trien-3-ol; or functional derivatives or functional analogues thereof.

In some embodiments, an estrogen is a natural or synthetic estrogen, whose action occurs in all estrogen-receptor-containing organs and systems, i.e. practically the entire body. However since these estrogens can cause great cell proliferation in tissues of the female genital tract (endometrium) and breast gland epithelium, in some embodiments, the administration of the composition comprising an estrogen or estrogen mimetic is localized to the tumor location or administered locally to the tumor.

Due to the proliferative effects of estrogens being linked to a benign prostate hyperplasia and/or gynecomastia in man (C. Knabbe, "Endocrine Therapy of Prostate Disease", in B. Allolio, H. M. Schulte (eds.), Practical Endocrinology, Urban & Schwarzenberg, Munchen, 645 to 651, 1996), estrogen therapy or replacement in man, has never been seriously considered. However, the present invention encompasses treatment with estrogen or an estrogen mimetic of a male subject with mesothelioma, where the male subject has been identified to have expression of RERG at or above a reference level as disclosed herein.

In some embodiments, the methods to treat mesothelioma as disclosed herein can comprise administration of a composition comprising an estrogen and an estrogen mimetic and an additional agent and/or additional therapy. Tumor treatments often comprise more than one therapy. As such, in certain embodiments the present invention provides methods for treating mesothelioma comprising administering to a subject in need thereof a pharmaceutical composition of the present invention, and further comprising administering at least one additional therapy.

In some embodiments, the methods of the present invention further comprise administering to the subject at least one additional therapy, concurrently with, subsequently, or prior to the treatment with the estrogen or estrogen agent. In some embodiments, an additional therapy is chemotherapy In certain embodiments, an additional therapy may also be designed to treat mesothelioma. An additional therapy may be a chemotherapeutic agent. In some embodiments, the chemotherapeutic agent may be, but is not limited to, cisplatin, pemetrexed, navelbine, gemcitabine, carboplatin, camptothecins, doxorubicin, cyclophosphamide, etoposide, vinblastine, Actinomycin D and cloposide. In some embodiments, an additional therapy may be a small molecule or antibody, which may, in some embodiments, interfere with a receptor, or other molecule involved in necessary survival, proliferation, or invasion pathways in the disease. In some embodiments, the small molecule or antibody may be, but is not limited to, vorinostat, a PI3 kinase inhibitor, a mTOR inhibitor, a proteosome inhibitor, a vascular targeting agent, or an angiogenesis inhibitor. In some embodiments, an additional therapy may be the use of radiation.

In some embodiments, an additional therapy is a compound currently used to treat mesothelioma, for example, current therapeutic options include the use of pemetrexed (marketed under the trademark ALIMTA®) as a single agent, that has demonstrated a moderate response rate of 14.1% and a median overall survival of 10.7 months [Scagliotti G V, Shin D M, Kindler H L, Vasconcelles M J, Keppler U, Manegold C, et al. J Clin Oncol 2003; 21 (8):1556-1561] or combinations with platinum derivatives (cisplatin or carboplatin) plus pemetrexed [Castagneto B, Botta M, Aitini E, Spigno F, Degiovanni D, Alabiso O, et al. Ann Oncol 2008; 19:370-373].

In some embodiments, an additional therapy is a chemotherapeutic agent. In some embodiments, the chemotherapeutic agent is selected from the group consisting of cisplatin, pemetrexed, navelbine, gemcitabine, carboplatin, camptothecins, doxorubicin, cyclophosphamide, etoposide, vinblastine, Actinomycin D and cloposide. In some embodiments, said additional therapy is a small molecule or antibody. In some embodiments, said small molecule or antibody includes but is not limited to vorinostat, PI3 kinase inhibitors, mTOR inhibitors, proteosome inhibitors, vascular targeting agents, angiogenesis inhibitors. In some embodiments, said additional therapy further comprises radiation therapy. In some embodiments, said additional therapy further comprises adjuvant immunological treatments. In other embodiments, said adjuvant immunological treatments may be selected from the group consisting of interferon and interleukin.

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In certain such embodiments, the additional therapy is selected to treat or ameliorate a side effect of one or more pharmaceutical compositions of the present invention. Such side effects include, without limitation, injection site reactions, liver function test abnormalities, renal function abnormalities, liver toxicity, renal toxicity and central nervous system abnormalities.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, suitable administration routes of a pharmaceutical composition comprising an estrogen or estrogen mimetic for the treatment of mesothelioma include, but are not limited to, oral, buccal, intradermal, transdermal, rectal, transmucosal, intestinal, enteral, topical, suppository, through inhalation, intratracheal, intrathecal, intraventricular, intraperitoneal, intrapleural, intrapericardial, intranasal, intraocular, intratumoral, and parenteral (e.g., intravenous, intramuscular, intramedullary, and subcutaneous). An additional suitable administration route includes chemoembolization. In certain embodiments, pharmaceutical intrathecals are administered to achieve local rather than systemic exposures. For example, pharmaceutical compositions may be injected directly in the area of desired effect (e.g., into a tumor). In some embodiments, the administration route is via the skin, e.g., a patch, e.g., a skin patch or by a cream and the like. Estrogen skin patches are well known by persons of ordinary skill in the art.

In certain embodiments, a pharmaceutical composition of the present invention is administered in the form of a dosage unit (e.g., tablet, capsule, bolus, etc.). In certain embodiments, such pharmaceutical compositions comprise a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, the compositions of the present invention comprising an estrogen or estrogen mimetic may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously interact with the formulation.

In certain embodiments, pharmaceutical compositions of the present invention comprising an estrogen or estrogen mimetic can comprise one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulosem and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, granule, tablet, and/or capsule). In certain of such embodiments, a solid pharmaceutical composition is prepared using ingredients known in the art, including, but not limited to, starches, sugars, diluents, granulating agents, lubricants, binders, and disintegrating agents.

In certain embodiments, a pharmaceutical composition of the present invention comprising an estrogen or estrogen mimetic can be formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprising an estrogen or estrogen mimetic comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant POLYSORBATE 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprising an estrogen or estrogen mimetic comprises a sustained-release system. A non-limiting example of such a sustained-release system is a semipermeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition comprising an estrogen or estrogen mimetic is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multidose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition comprising an estrogen or estrogen mimetic is prepared for transmucosal administration. In certain of such embodiments penetrants appropriate to the barrier to be permeated are used in the formulation. Such penetrants are generally known in the art.

In certain embodiments, a pharmaceutical composition comprising an estrogen or estrogen mimetic is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition comprising an estrogen or estrogen mimetic is prepared for rectal administration, such as a suppositories or retention enema. Certain of such pharmaceutical compositions comprise known ingredients, such as cocoa butter and/or other glycerides.

In certain embodiments, a pharmaceutical composition comprising an estrogen or estrogen mimetic is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment. As discussed herein, a topical administration can be via a skin patch, ointment or cream or the like.

In certain embodiments, the therapeutically effective amount of the pharmaceutical composition of the present invention is sufficient to prevent, alleviate or ameliorate symptoms of a disease or to prolong the survival of the subject being treated. Determination of a therapeutically effective amount is well within the capability of those skilled in the art.

In certain embodiments, the pharmaceutical composition of the present invention comprising an estrogen or estrogen mimetic can be formulated as a prodrug. In certain embodiments, upon in vivo administration, a prodrug is chemically converted to the biologically, pharmaceutically or therapeutically more active form of the composition. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Methods and Assays for Determining Mesothelioma Prognosis

In some embodiments, the methods, systems and assays as disclosed herein provide a forecast or prediction (e.g., prognosis) of the probable course or outcome of the mesothelioma and responsiveness to its treatment. As used herein, cancer or mesothelioma prognosis includes distinguishing between cancer stages and subtypes, and the forecast or prediction of any one or more of the following: duration of survival of a patient susceptible to or diagnosed with a cancer, duration of recurrence-free survival, time to disease relapse, duration of progression-free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. As used herein, "prognostic for cancer" means providing a forecast or prediction of the probable course or outcome of the cancer, e.g., mesothelioma. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer.

In some embodiments, the assays described herein relate to determining whether a subject has an increased likelihood of having a good prognosis and/or improved survival after diagnosis of mesothelioma. As used herein, the term "good prognosis" refers to a cancer that is likely to be responsive to treatment with an estrogen or estrogen mimetic as disclosed herein. As used herein, the term "poor prognosis" can refer to a cancer that has metastasized in a subject or is likely to metastasize in a subject, including malignant tumors with high potential for metastasis (mesothelioma cancer that is considered to be aggressive). The term "improved survival time" refers to the time of survival after diagnosis. Herein, the inventors have demonstrated that female subjects with an expression level of RERG at or above a reference level have a median prolonged life of approximately 9-25 months longer than the life expectancy or survival of female subjects that have low expression of RERG (e.g., below the reference level). Accordingly, the present invention provides for assays and methods to identify mesothelioma subjects that have an improved survival time, and/or good prognosis.

As disclosed herein in the Examples, the inventors surprisingly discovered that when the survival or longevity of a population of subjects with mesothelioma is assessed, approximately the top 50% longest surviving subjects had increased expression of RERG as compared to the remaining population (e.g., the 50% with the shortest survival). In particular, the top half (e.g., the cohort of subjects with the longest survival) always did significantly better than the bottom half. This was particularly apparent in female subjects with mesothelioma.

In some embodiments, the present invention provides an assay for determining the survival time of a subject with mesothelioma, and/or the prognostic forecast of a subject with mesothelioma. In some embodiments, an assay comprises: (i) contacting a biological sample from a subject with an affinity binding molecule which binds to the Ras-like, estrogen-regulated, growth inhibitor (RERG) protein or the RERG gene product; (ii) measuring the amount of affinity binding molecule which is bound to the RERG protein or RERG gene product (e.g., RERG); and (iii) comparing the measured levels with a reference level, and where a level of the affinity binding molecule which is bound to the RERG protein or RERG gene product is at the same level or above a reference level, it indicates that the subject has an increased probability of good prognosis and improved survival time, or increased overall survival time after a diagnosis of mesothelioma, whereas, if and the level of the affinity binding molecule which is bound to the RERG protein is below the reference level, it indicates that the subject has an increased probability of a poor prognosis and decreased survival time or decreased overall survival time after a diagnosis with mesothelioma.

In another embodiment, the present invention encompasses an assay comprising: (i) measuring or quantifying the amount of Ras-like, estrogen-regulated, growth inhibitor (RERG) protein or gene expression product in a biological subject obtained from the subject, (ii) comparing the measured or quantified amount of RERG protein or gene expression product with a reference value, (iii) identifying the subject as having an increased probability of a good prognosis and improved survival time or increased overall survival time if the amount of RERG protein or gene expression product is the same as, or increased relative to the reference value, or identifying the subject has having an increased probability of a poor prognosis and decreased survival time (or decreased overall survival time) if the amount of RERG protein or gene expression product is decreased relative to the reference value.

Another embodiment of the present invention relates to an assay comprising: (a) contacting a biological sample from a subject with at least one RERG specific antibody or at least one RERG specific probe; wherein the RERG specific antibody or RERG probe comprises a detectable label or means of generating a detectable signal, (b) detecting the presence or intensity of a detectable signal associated with RERG specific antibody or RERG probe which indicates the level of the RERG protein or RERG gene product (e.g., mRNA); where an increased level, or the same level of RERG protein or RERG gene product (as indicated by the detectable signals), relative to a reference level indicates the subject has a probability of a good prognosis and improved survival time or increased overall survival time after a diagnosis of mesothelioma, whereas a decreased level of RERG protein or gene expression product (as indicated by the detectable signals), relative to a reference level, indicates an increased probability of a poor prognosis and decreased survival time or decreased overall survival time after a diagnosis with mesothelioma.

Another aspect of the present invention relates to an assay to determine if a subject with mesothelioma will benefit from treatment with an estrogen therapy, e.g., an estrogen or estrogen mimetic as disclosed herein, the assay comprising: (a) contacting a biological sample obtained from the subject with at least one an affinity binding molecule which binds to the Ras-like, estrogen-regulated, growth inhibitor (RERG) protein or the RERG gene product; (b) measuring the amount of affinity binding molecule which is bound to the RERG protein or RERG gene product, where an increased, or the same level of RERG protein or RERG gene product relative to a reference level for the RERG protein or RERG gene product (e.g., mRNA) indicates the subject will benefit from treatment with estrogen therapy.

In some embodiments, if the level of the RERG protein and/or RERG mRNA is increased relative to a reference level of the RERG protein and/or RERG mRNA by a statistically significant level, it indicates the subject with mesothelioma will benefit from estrogen therapy, e.g., an estrogen or estrogen mimetic as disclosed herein. In some embodiments, if the level of the RERG protein and/or RERG mRNA is increased relative to a reference level of the RERG protein and/or RERG mRNA by a statistically significant level, the subject has an increased probability of a good prognosis and/or increased overall survival after surgery as compared to a subject who has a RERG expression level below the reference level. In some embodiments, the reference level is an average REGR expression level in a comparable biological sample (e.g., matched by gender, tissue type etc.) from a population of mesothelioma subjects with a median overall survival time after surgery mesothelioma.

In some embodiments, if the level of the RERG protein and/or RERG mRNA is at least about 0.5-fold, or at least about 0.5-fold, or at least about 1-fold, or at least about 1.25-fold, or at least about 1.5-fold or at least about 1.75 fold, or at least about 2-fold (e.g. 2×) greater than the reference level, e.g. at least 2×, at least 3×, at least 4×, at least 5×, at least 6×, or greater than the reference level, it indicates the subject will likely benefit from treatment with estrogen therapy. In some embodiments, a RERG expression level measured in a subject which is at least about 0.5-fold, or at least about 0.5-fold, or at least about 1-fold, or at least about 1.25-fold, or at least about 1.5-fold or at least about 1.75 fold, or at least 2.5-fold, or at least about 3-fold or at least about 3.5 fold, or greater than 3.5 fold higher than the reference level indicates that the subject has an increased probability of a good prognosis and/or increased overall survival after surgery as compared to a subject who has a RERG expression level below the reference level. In some embodiments, a level of the RERG protein and/or RERG mRNA can be increased relative to a reference level if the level of the RERG protein and/or RERG mRNA is at least 3× of the reference level.

In some embodiments, a level of the RERG protein and/or RERG mRNA can be increased relative to a reference level if the level of the RERG protein and/or RERG mRNA from the biological sample from the subject is higher by a statistically significant level than the reference RERG mRNA or protein level, or is at least about 10%, or at least about 15% or more than 15% increased (e.g., higher) as compared to the reference level, e.g. at least about 10%, or at least about 15%, at least 20%, at least 25%, at least 30% or more higher than the reference level. In some embodiments, a level of the RERG protein and/or RERG mRNA can be increased relative to a reference level if the RERG protein and/or RERG mRNA in the biological sample is at least 50% greater than the reference level, or e.g. at least 50%, at least 55%, at least 60%, at least 65% or more greater than the level of the RERG protein and/or RERG mRNA in the reference sample. In some embodiments, a level of the RERG protein and/or RERG mRNA can be increased relative to a reference level if the level of the RERG protein and/or RERG mRNA in the biological sample from the subject is a least 25% greater than the level of the RERG protein and/or RERG mRNA in the reference sample, e.g. at least 25%, at least 30%, at least 35%, at least 40% or more greater level of the RERG protein and/or RERG mRNA in the biological sample from the subject as compared to the reference level.

In some embodiments, a level of RERG protein or RERG mRNA measured in a biological sample obtained from a subject is identified to have mesothelioma with a good prognosis and/or increased overall survival if the levels are increased relative to a reference level for RERG protein or RERG mRNA by at least about 0.5-fold, or at least about 0.5-fold, or at least about 1-fold, or at least about 1.25-fold, or at least about 1.5-fold or at least about 1.75 fold, or at least 2× of the reference level, e.g. at least 2×, at least 2.5×, at least 3×, at least 3.5×, at least 4×, at least 5×, at least 6×, or greater of the reference level. In some embodiments, a level of RERG protein or RERG mRNA in a subject who is identified to have mesothelioma with a good prognosis and/or increased overall survival is by at least 3× of the reference level. In some embodiments, a level of RERG protein or RERG mRNA in a subject who is identified to have to have mesothelioma with a good prognosis and/or increased overall survival has a RERG protein or RERG mRNA level that is at least 15% higher than the reference level, e.g. at least 15%, at least 20%, at least 25%, at least 30% or more higher (or increased) relative to the reference level. In some embodiments, a level of RERG protein or mRNA in subject who is identified to have mesothelioma with a good prognosis and/or increased overall survival has a level of RERG protein or RERG mRNA increased relative to a reference level by at least 50%, e.g., increased by at least 50%, at least 55%, at least 60%, at least 65% or more. In some embodiments, a level of RERG protein or mRNA in subject who is identified to have mesothelioma with a good prognosis and/or increased overall survival has a level of RERG protein or RERG mRNA increased relative to a reference level by at least 25%, at least 30%, at least 35%, at least 40% or more than the reference level.

In some embodiments, an affinity binding molecule which binds the RERG protein is a protein-binding molecule. In some embodiments, a protein binding molecule is an antibody or antibody fragment or a protein which comprises an antibody binding domain.

In some embodiments, a RERG protein can be detected using a RERG-specific antibody reagent, i.e. an antibody reagent that binds specifically to RERG as compared to other proteins present in the sample. In some embodiments, antibody reagents, e.g. antibodies, monoclonal and chimeric antibodies useful in the methods as disclosed herein can be manufactured using well-known methods, e.g., as described in Howard and Kaser "Marking and Using Antibodies: A Practical Handbook" CRC Press (2006); which is incorporated by reference herein in its entirety.

Detection of the presence of RERG protein and/or determination of the level of RERG protein as described herein can be according to any method known in the art. Immunological methods to detect RERG protein in accordance with the present technology include, but are not limited to antibody techniques such as immunohistochemistry, immunocytochemistry, flow cytometry, fluorescent-activated cell sorting (FACS), immunoblotting, radioimmunoassays, western blotting, immunoprecipitation, enzyme-linked immunosorbent assays (ELISA), and derivative techniques that make use of antibody reagents as described herein.

In some embodiments, detection of the expression of RERG and/or determination of RERG protein can be performed using flow cytometry. In some embodiments, detection of the expression of RERG and/or determination of RERG protein can be performed using immunochemical methods and immunocytological methods, e.g. ELISA and other immunoblotting or immunosorbant assays.

Immunochemistry is a family of techniques based on the use of a specific antibody, wherein antibodies are used to specifically target molecules inside or on the surface of cells. In some embodiments, immunohistochemistry ("IHC") and immunocytochemistry ("ICC") techniques can be used to detect or measure the levels of RERG protein. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for the RERG protein. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010): Lin and Prichard "Handbook of Practical Immunohistochemistry" Springer (2011); which are incorporated by reference herein in their entireties. In some embodiments, immunocytochemistry may be utilized where, in general, tissue or cells are obtained from a subject are fixed by a suitable fixing agent such as alcohol, acetone, and paraformaldehyde, to which is reacted an antibody. Methods of immunocytological staining of human samples is known to those of skill in the art and described, for example, in Burry. "Immunocytochemistry: A Practical Guide for Biomedical Research" Springer (2009); which is incorporated by reference herein in its entirety.

Immunochemical methods can include the use of two or more antibodies which will produce a detectable signal only when they are colocalized, e.g. fluorescence resonance energy transfer (FRET) or bioluminescence resonance energy transfer (BRET). FRET and BRET are well known in the art (see, e.g. Daunert and Deo, Eds. "Photoproteins in Bioanalysis" Wiley-VCH: 2006 and Perisamy and Day, Eds. "Molecular Imaging: FRET Microscopy and Spectroscopy" Oxford University Press: 2005: which are incorporated by reference herein in their entireties).

In some embodiments, the assays, methods, and/or systems described herein can comprise: contacting a sample obtained from a subject with a first antibody reagent which is conjugated to a solid support, contacting the sample with a second, detectable antibody reagent, detecting a signal from the second antibody reagent, wherein the presence of a signal from the second antibody reagent indicates the presence or level of RERG protein. In some embodiments, after the contacting steps, the sample can be washed to remove unbound antibody reagents not bound to the first antibody reagent. In some embodiments, the first antibody reagent can be detectably labeled. In some embodiments, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") cells for which it is specific (e.g. RERG protein). The solid support can then be contacted with a second labeled antibody reagent (e.g. a detection antibody reagent). The detection antibody reagent can, e.g. comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to a cell or group of cells, i.e. the presence of a signal indicates the presence of the RERG protein. Between each step the plate is typically washed with a mild detergent solution to remove any proteins or antibodies that are not specifically bound. After the final wash step the plate is developed by adding an enzymatic substrate to produce a visible signal, which indicates the quantity or level of RERG protein in the sample. Older ELISAs utilize chromogenic substrates, though newer assays employ fluorogenic substrates with much higher sensitivity. In some embodiments, one of the antibody reagents can be a RERG-specific antibody reagent. There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem. 22:895-904. These references are hereby incorporated by reference in their entirety.

In one embodiment, the assays, systems, and methods described herein can comprise a lateral flow immunoassay test (LFIA), also known as the immunochromatographic assay, or strip test to measure or determine the level of RERG protein in a sample. LFIAs are a simple device intended to detect the presence (or absence) or level of RERG protein in a sample. There are currently many LFIA tests are used for medical diagnostics either for home testing, point of care testing, or laboratory use. LFIA tests are a form of immunoassay in which the test sample flows along a solid substrate via capillary action. After the sample is applied to the test it encounters a colored antibody reagent which mixes with the sample, and if bound to a portion of the sample, transits the substrate encountering lines or zones which have been pretreated with a second antibody reagent. Depending upon the level of RERG protein present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be use on site in the field. LFIA tests can be operated as either competitive or sandwich assays. Sandwich LFIAs are similar to sandwich ELISA. The sample first encounters colored particles which are labeled with antibody reagents specific for a target (e.g. RERG protein). The test line will also contain antibody reagents (e.g. RERG protein). The test line will show as a colored band in positive samples. In some embodiments, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i.e. the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports have been described in the art in the context of an immunoassay for a number of antigen biomarkers. U.S. Pat. Nos. 4,943,522; 6,485,982; 6,187,598; 5,770,460; 5,622,871; 6,565,808, U.S. patent application Ser. No. 10/278,676; U.S. Ser. No. 09/579,673 and U.S. Ser. No. 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technology for the detection of levels of RERG protein.

Further examples of protocols which can be used in the methods, assays, and systems described herein to the expression level of RERG are described in U.S. Pat. No. 6,586,259; Li et al. Cytometry. 1999 35:154-161; and Hagberg and Lyberg. Platelets. 2000 11:151-160; which are incorporated herein by reference in their entireties. In some embodiments, one or more of the antibody reagents described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the antibody reagent. Alternatively, a detectable label can be linked such as by directly labeling a molecule that achieves binding to the antibody reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection antibody is label with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfiuorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes.

In some embodiments, a detectable label can be a radio-label including, but not limited to $^3$H, $^{125}$I, $^{35}$S, $^{14}$C, $^{32}$P, and $^{33}$P.

In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In some embodiments, a detectable label is a chemiluminescent label, including, but not limited to lucigenin, luminol, luciferin, isoluminol, theromatic acridinium ester, imidazole, acridinium salt and oxalate ester.

In some embodiments, a detectable label can be a spectral colorimetric label including, but not limited to colloidal gold or colored glass or plastic (e.g., polystyrene, polypropylene, and latex) beads.

In some embodiments, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e.g. from DAKO; Carpinteria, Calif.

An antibody reagent can also be detectably labeled using fluorescence emitting metals such as $^{152}$Eu, or others of the lanthanide series. These metals can be attached to the antibody reagent using such metal chelating groups as diethylenetriaminepentaacetic acid (DTPA) or ethylenediaminetetraacetic acid (EDTA).

In some embodiments, wherein at least two different antibody reagents are used, the different types of antibody reagents can be labeled with different detectable labels. Two detectable labels are considered different if the signal from one label can be distinguished from the signal from the other.

In some embodiments, the detection of RERG protein is by FACS. Flow cytometry is a well-known technique for analyzing and sorting cells (or other small particles) suspended in a fluid stream. This technique allows simultaneous analysis of the physical and/or chemical characteristics of single cells flowing through an optical, electronic, or magnetic detection apparatus. As applied to FACS, the flow cytometer consists of a flow cell which carries the cells in a fluid stream in single file through a light source with excites the fluorescently labeled detection marker(s) (for example, antibody reagents) and measures the fluorescent character of the cell. The fluid stream is then ejected through a nozzle and a charging ring, under pressure, which breaks the fluid into droplets. The flow cell device and fluid stream is calibrated such that there is a relatively large distance between individual cells or bound groups of cells, resulting in a low probability that any droplet contains more than a single cell or bound group of cells. The charging ring charges the droplets based on the fluorescence characteristic of the cell which is contained therein. The charged droplets are then deflected by an electrostatically-charged deflection system which diverts the droplets into various containers based upon their charge (related to the fluorescence intensity of the cell). A FACS system (e.g. the FACSARIA™ flow cytometer (BD Biosciences) and FLOWJO™ Version 7.6.4 (Tree-Star) as used in the Examples described herein) can detect and record the number of total cells as well as the number of cells which display one or more fluorescent characteristics.

In some embodiments, a method, assay, and/or system as described herein can comprise: contacting a sample obtained from a subject with a detectable RERG-specific antibody reagent (comprising a first distinguishable, detectable label), determining whether the distinguishable signals produced by the labels; In some embodiments, after the contacting step, the sample can be washed to remove the unbound antibody reagents.

In some embodiments, the level of RERG expression can be determined using high-throughput FACS (see, e.g. US Patent Publication 2009/0239235 describing a technology commercially available as FACSCANTO™ from BD Biosciences and which is incorporated by reference herein in its entirety).

In some embodiments, the level of RERG expression can be determined using a known system for automated protein expression level determination, including for example, but not limited to, mass spectrometry systems including Matrix Assisted Laser Desorption Ionization—Time of Flight (MALDI-TOF) systems and SELDI-TOF-MS ProteinChip array profiling systems; systems for analyzing gene expression data (see, for example, published U.S. Patent Application, Pub. No. U.S. 2003/0194711, which is incorporated herein in its entirety by reference); systems for array based expression analysis: e.g., HT array systems and cartridge array systems such as GENECHIP® AUTOLOADER, COMPLETE GENECHIP® Instrument System, GENECHIP® Fluidics Station 450, GENECHIP® Hybridization Oven 645, GENECHIP® QC Toolbox Software Kit, GENECHIP® Scanner 3000 7G plus Targeted Genotyping System, GENECHIP® Scanner 3000 7G Whole-Genome Association System, GENETITAN™ Instrument, and GENECHIP® Array Station (each available from Affymetrix, Santa Clara, Calif.); automated ELISA systems (e.g., DSX® or DS2® (available from Dynax, Chantilly, Va.) or the TRITURUS® (available from Grifols USA, Los Angeles, Calif.), The MAGO® Plus (available from Diamedix Corporation, Miami, Fla.); Densitometers (e.g. X-Rite-508-SPECTRO DENSITOMETER® (available from RP IMAGING™, Tucson, Ariz.), The HYRYS™ 2 HIT densitometer (available from Sebia Electrophoresis, Norcross, Ga.); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, (available from Becton Dickinson, Franklin Lakes, N.J.); and radio isotope analyzers (e.g. scintillation counters).

In some embodiments, the level of RERG expression can be determined using a nucleic acid probe which binds to a target RERG mRNA. Accordingly, in some embodiments, an affinity binding molecule which binds to a RERG mRNA is a nucleic acid binding molecule, such as but not limited to a nucleic acid probe. In embodiments where the level of RERG expression measured in a biological sample is a gene product, or isoform gene transcript, such as levels of mRNA, such measurements are commonly performed using DNA or RNA collected from biological samples, e.g., tissue biopsies, urine, stool, sputum, blood, cells, tissue scrapings, breast aspirates or other cellular materials, and can be performed by a variety of methods commonly known in the art, including, but not limited to, PCR, RT-PCR, quantitative RT-PCR (QRT-PCR), isoform-specific QRT-PCR, hybridization with isoform-specific probes.

In alternative embodiments, amplification methods to detect levels of RERG mRNA (e.g., isoforms of RERG mRNA) encompassed for use in the methods as disclosed herein, and include for example but are not limited to: PCR, ligation chain reaction (LCR) (see, e.g., Landegran, et al., 1988. Science 24 1: 1 077-1 080; and Nakazawa, et al., 1994. Proc. Natl. Acad. Sci, USA 91:360-364), self sustained sequence replication (see, Guatelli, et al., 1990. Proc. Natl. Acad. Sci. USA 87: 1874-1 878), transcriptional amplification system (see, Kwoh, et al., 1989. Proc. Natl. Acad. Sci. USA 86: 1 173-1 177); Qb Replicase (see, Lizardi, et al, 1988. BioTechnology 6:1 197), or any other nucleic acid amplification method, followed by the detection of the amplified molecules using techniques well known to those of skill in the art. These detection schemes are especially useful for the detection of nucleic acid molecules if such molecules are present in very low numbers.

The assays and methods as described herein can relate to determining if a subject has an increased level of RERG protein and/or RERG mRNA relative to a reference level. In some embodiments, the reference level can comprise the level of RERG protein and/or RERG gene product (e.g. mRNA) in a sample of the same type taken from a subject not exhibiting any signs or symptoms of mesothelioma. In some embodiments, the reference level of the RERG protein and/or RERG mRNA can be the level of RERG in a healthy subject not having, or not diagnosed as having, mesothelioma. In some embodiments, the reference level of the RERG protein and/or RERG mRNA can be the level in a sample of similar cell type, sample type, sample processing, and/or obtained from a subject of similar age, sex and other demographic parameters as the sample/subject for which the level of the RERG protein and/or RERG mRNA is to be determined. In some embodiments, the a test biological sample and control reference sample are of the same type, that is, obtained from the same biological source, and comprising the same composition, e.g. the same number and type of cells.

The term "sample" or "test sample" to "biological sample" as used herein denotes a sample taken or isolated from a biological organism, e.g., a blood sample from a subject or a tissue sample, e.g., a biopsy tissue sample. Exemplary biological samples include, but are not limited to, whole blood; peripheral blood; whole peripheral blood; a nasal polyp; etc. The term also includes a mixture of the above-mentioned samples. The term "test sample" or "biological sample" also includes untreated or pretreated (or pre-processed) biological samples. In some embodiments, a test sample can comprise cells from subject. In some embodiments, a test sample can comprise mesothelioma cells or cancer cells. In some embodiments, the biological sample is a biopsy sample, e.g., a lung biopsy sample, or a blood sample. In some embodiments, the biological sample has been frozen.

In some embodiments, the sample can comprise a biological tissue selected from the group consisting of: whole blood; peripheral blood; whole peripheral blood; tissue sample, biopsy sample, a nasal polyp; and products thereof. In some embodiments, the sample can comprise any tissue affected by, or suffering from symptoms, or display markers of mesothelioma, e.g. the sample can comprise bronchial biopsies and/or gastrointestinal samples.

The test sample or biological sample can be obtained by removing a sample of cells from a subject, for example, a blood sample or tissue biopsy sample, but can also be accomplished by using previously isolated cells (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of RERG protein or RERG gene product (e.g., mRNA) as described herein.

In some embodiments, the methods, assays, and systems described herein can further comprise a step of obtaining a test sample or biological sample from a subject.

In some embodiments, the methods, assays, and systems described herein can comprise creating a report based on the level of RERG protein or RERG gene product (e.g., mRNA). In some embodiments, the report denotes raw values of the number/level of expression of the RERG protein or mRNA in the biological sample, or it indicates a percentage or fold increase of expression of the RERG protein or mRNA as compared to a reference level, and/or provides a signal that the subject has an increased probability of having a good prognosis and/or increased overall survival time.

The methods, assays, and systems described herein can relate to methods of treatment, methods of determining if a subject can benefit from certain therapies, e.g., if a subject is responsive to estrogen therapy.

In some embodiments, aspects of the present invention relate to methods of identifying a subject with mesothelioma who would benefit from treatment with an estrogen or estrogen mimetic according to the methods as disclosed herein.

In some embodiments, the methods described herein relate to treating a subject with mesothelioma who has been determined to have expression of RERG protein or mRNA above a reference level with an estrogen therapy, e.g., an estrogen or estrogen mimetic. Subjects having respiratory disease can be identified by a physician using current methods of diagnosing mesothelioma. Symptoms and/or complications of mesothelioma which characterize these conditions and aid in diagnosis are well known in the art and include but are not limited to, wheezing, coughing, difficulty breathing, tightness in the chest, and nocturnal worsening of symptoms. Tests that may aid in a diagnosis of mesothelioma include, but are not limited to, pulmonary function tests, exhaled nitric oxide test, or tests to rule out other conditions (e.g. x-rays and/or CT scans to rule out COPD or congestive heart failure). A history of exposure to asbestos can also aid in determining if a subject is likely to have mesothelioma or in making a diagnosis. Symptoms of mesothelioma include, but are not limited to anemia, blood clotting disorder, bowel obstruction, chest pain, persistent dry or raspy cough, coughing up blood (hemoptysis), shortness of breath (dyspnea), pain in the lower back or rib area, painful breathing, development of lumps under the skin on the chest, difficulty with swallowing (dysphagia), night sweats or fever, nausea, unexplained weight loss, fatigue, abdomen, pericardium, peritoneal and/or pleural effusion.

The compositions and methods described herein can be administered to a subject with mesothelioma having or diagnosed as having a level of RERG expression at or above a reference value. In some embodiments, the methods described herein comprise administering an effective amount of compositions described herein, e.g. an estrogen or estrogen mimetic as disclosed herein to a subject in order to alleviate a symptom of mesothelioma and/or to increase the overall survival time as compared to a subject not administered an estrogen or estrogen mimetic as disclosed herein. As used herein, "alleviating a symptom of mesothelioma" is ameliorating any condition or symptom associated with mesothelioma. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral and airway (aerosol), administration. Administration can be local or systemic.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an estrogen or estrogen mimetic which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, an effective dose of a composition comprising an estrogen or estrogen mimeric as described herein can be administered to a patient once. In certain embodiments, an effective dose of a composition comprising an estrogen or estrogen mimeric can be administered to a patient repeatedly. For systemic administration, subjects can be administered a therapeutic amount of a composition comprising an estrogen or estrogen mimeric such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. A composition comprising an estrogen or estrogen mimeric can be administered over a period of time, such as over a 5 minute, 10 minute, 15 minute, 20 minute, or 25 minute period. The administration can be repeated, for example, on a regular basis, such as hourly for 3 hours, 6 hours, 12 hours or longer or such as biweekly (i.e., every two weeks) for one month, two months, three months, four months or longer.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. mesothelioma by at least 10%, at least 15%, at least 20%, at least 25%, at least 30%, at least 40%, at least 50%, at least 60%, at least 70%, at least 80% or at least 90% or more.

The dosage of a composition comprising an estrogen or estrogen mimeric as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the therapeutic. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

Systems for Determining Prognosis of a Subject with Mesothelioma

In some aspects, the invention described herein is directed to systems (and computer readable media for causing computer systems) for obtaining data from at least one biological sample obtained from at least one subject, the system comprising 1) a determination module configured to receive the at least one biological sample from a subject with mesothelioma and perform at least one analysis on the at least one biological sample to determine the level of RERG expression (e.g., protein and/or mRNA expression); 2) a storage device configured to store data output from the determination module; and 3) a display module for displaying a content based in part on the data output from the determination module, wherein the content comprises a signal indicative of the level of RERG expression, and optionally the comparison of the level of the RERG expression levels from the biological sample obtained from the subject with a reference value for RERG expression.

Figure 9:
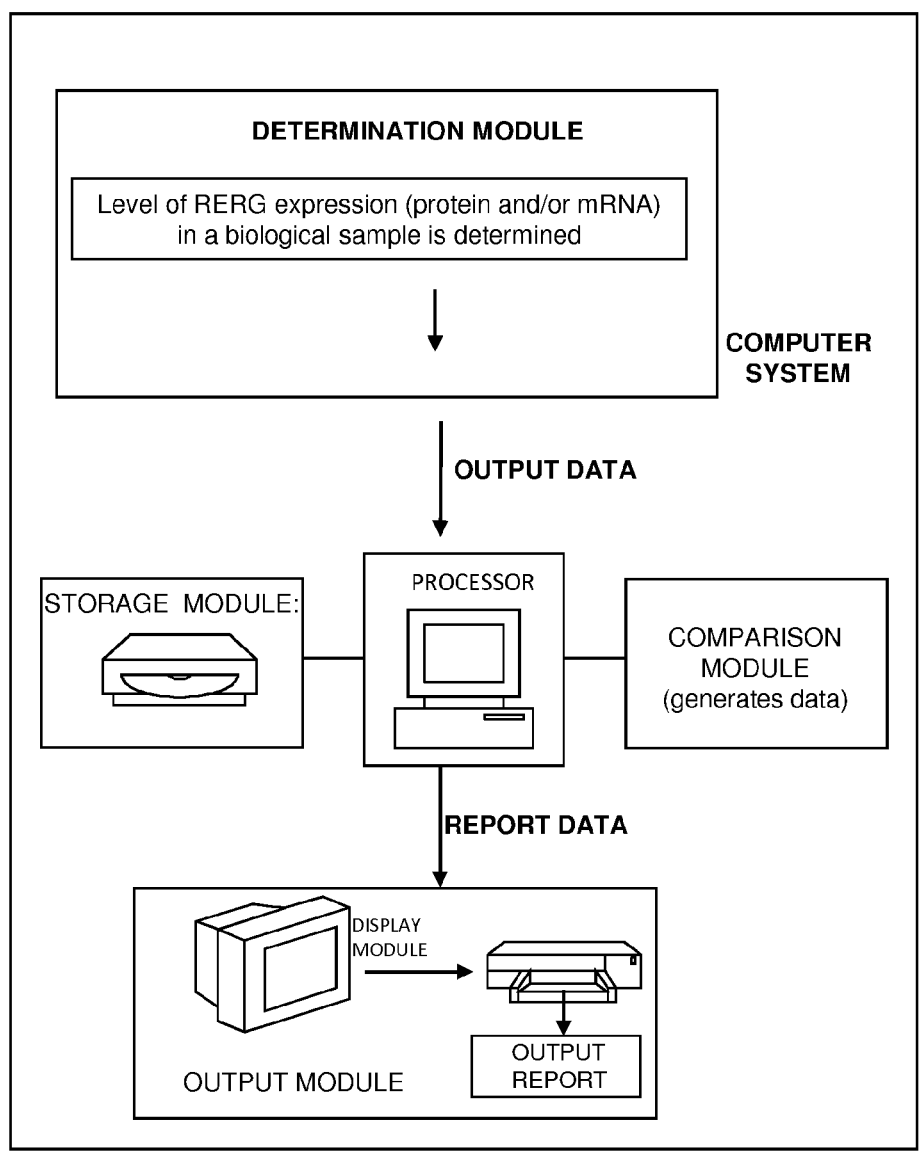
FIG. 9 is a diagram of an exemplary embodiment of a system for performing an assay for determining the levels of RERG expression (e.g., mRNA and/or protein levels) in a biological sample obtained from a mesothelioma subject.

In one embodiment, provided herein is a system comprising: (a) at least one memory containing at least one computer program adapted to control the operation of the computer system to implement a method that includes (i) a determination module configured to receive the at least one biological sample obtained from a subject with mesothelioma and perform at least one analysis on the at least one biological sample to determine the level of expression of RERG protein or mRNA in the biological sample; (ii) a storage module configured to store output data from the determination module; (iii) a computing module adapted to identify from the output data whether the level of RERG expression from the biological sample obtained from the subject indicates that the RERG expression is at the same level or above a reference value for RERG expression subjects and (iv) a display module for displaying a content based in part on the data output from the determination module, wherein the content comprises a signal indicative of the RERG expression and (b) at least one processor for executing the computer program (see FIG. 9).

In one embodiment, provided herein is a system comprising: (a) at least one memory containing at least one computer program adapted to control the operation of the computer system to implement a method that includes (i) a determination module configured to receive the at least one biological and/or test sample and perform at least one analysis on the at least one biological sample to determine the level of RERG expression in the sample; (ii) a storage module configured to store output data from the determination module; (iii) a computing module adapted to identify from the output data whether the level of expression of RERG protein or mRNA in the biological sample from a subject with mesothelioma obtained from a subject is the same level or above a reference level for RERG expression and indicates that the subject has an increased probability of a good prognosis and/or increased overall survival time (iv) a display module for displaying a content based in part on the data output from the determination module, wherein the content comprises a signal indicative of the level of RERG expression and (b) at least one processor for executing the computer program (see FIG. 9).

In some aspects, the invention described herein is directed to systems (and computer readable media for causing computer systems) for obtaining data from at least one sample obtained from at least one subject, the system comprising 1) a measuring module configured to measure the level of RERG protein and/or mRNA expression in a biological sample obtained from a subject, 2) a storage module configured to store output data from the measuring module, 3) a comparison module adapted to compare the data stored on the storage module with a reference level, and to provide a retrieved content, and 4) a display module for displaying whether the level of RERG expression in the test biological obtained from a subject is the same level, or greater, by a statistically significant amount, than the reference level and/or displaying the relative levels of RERG mRNA and/or protein.

In one embodiment, provided herein is a system comprising: (a) at least one memory containing at least one computer program adapted to control the operation of the computer system to implement a method that includes 1) a measuring module configured to measure the level of RERG expression (e.g., protein or mRNA expression) in a biological test sample obtained from a subject, 2) a storage module configured to store output data from the measuring module, 3) a computing module adapted to identify from the output data whether the level of RERG expression in the biological sample from the subject measured by the measuring module is the same level, or increased by a statistically significantly amount than a reference level, and 4) a display module for displaying a content based in part on the data output from the measuring module, wherein the content comprises a signal indicative of the level of RERG expression and (b) at least one processor for executing the computer program (see FIG. 9).

In some embodiments, the measuring module can measure the presence and/or intensity of a detectable signal from an immunoassay indicating the level of RERG protein in the test sample. In some embodiments, the measuring module can measure the presence and/or intensity of a detectable signal from an immunoassay indicating the presence RERG-specific antibody reagent in the test sample. Exemplary embodiments of a measuring module can include a FACS machine, automated immunoassay, etc.

The measuring module can comprise any system for detecting a signal elicited from an assay to determine the level of RERG protein or RERG mRNA as described above herein. In some embodiments, such systems can include an instrument, e.g., FACSARIA™ (BD Biosciences) as described herein for FACS analysis, or ELISA. In another embodiment, the measuring module can comprise multiple units for different functions, such as measurement of detectable signals from an affinity binding molecule, e.g., a RERG-specific antibody reagent and/or measurement of detectable signals from different affinity binding molecules, e.g., RERG specific nucleic acid probes. In one embodiment, the measuring module can be configured to perform the methods described elsewhere herein, e.g. FACS, RT-PCR, ELISA or detection of any detectable label or signal.

In some embodiments, the measuring system or a further module can be configured to process whole blood samples, e.g. to separate cells or portions of cells from whole blood for use in the assays described herein. In some embodiments, the measuring module can be configured to process tissue samples, e.g., biopsy samples. In some embodiments, the measuring module can be configured to process urine or other excreted biological sample from the subject.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip. The term a "computer system" may refer to a system having a computer, where the computer comprises a computer-readable medium embodying software to operate the computer. The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can be accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam. 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The functional modules of certain embodiments of the invention include at minimum a measuring module, a storage module, a computing module, and a display module. The functional modules can be executed on one, or multiple, computers, or by using one, or multiple, computer networks. The measuring module has computer executable instructions to provide e.g., levels of RERG expression levels (protein and/or mRNA) etc. in computer readable form.

The information determined in the measuring system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, biomolecule assayed and the level of said biomolecule. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In some embodiments of any of the systems described herein, the storage module stores the output data from the measuring module. In additional embodiments, the storage module stores reference information such as levels of RERG expression (protein and/or mRNA) in healthy subjects, subjects not having a cancer, e.g., not having mesothelioma and/or a population of subjects classified as having a good outcome or good prognosis and/or increased survival time after mesothelioma. In some embodiments, subjects classified as having good outcome or good prognosis have an increased survival time by about 9-months as compared to mesothelioma subjects with levels of RERG expression below the reference value.

Figure 10:
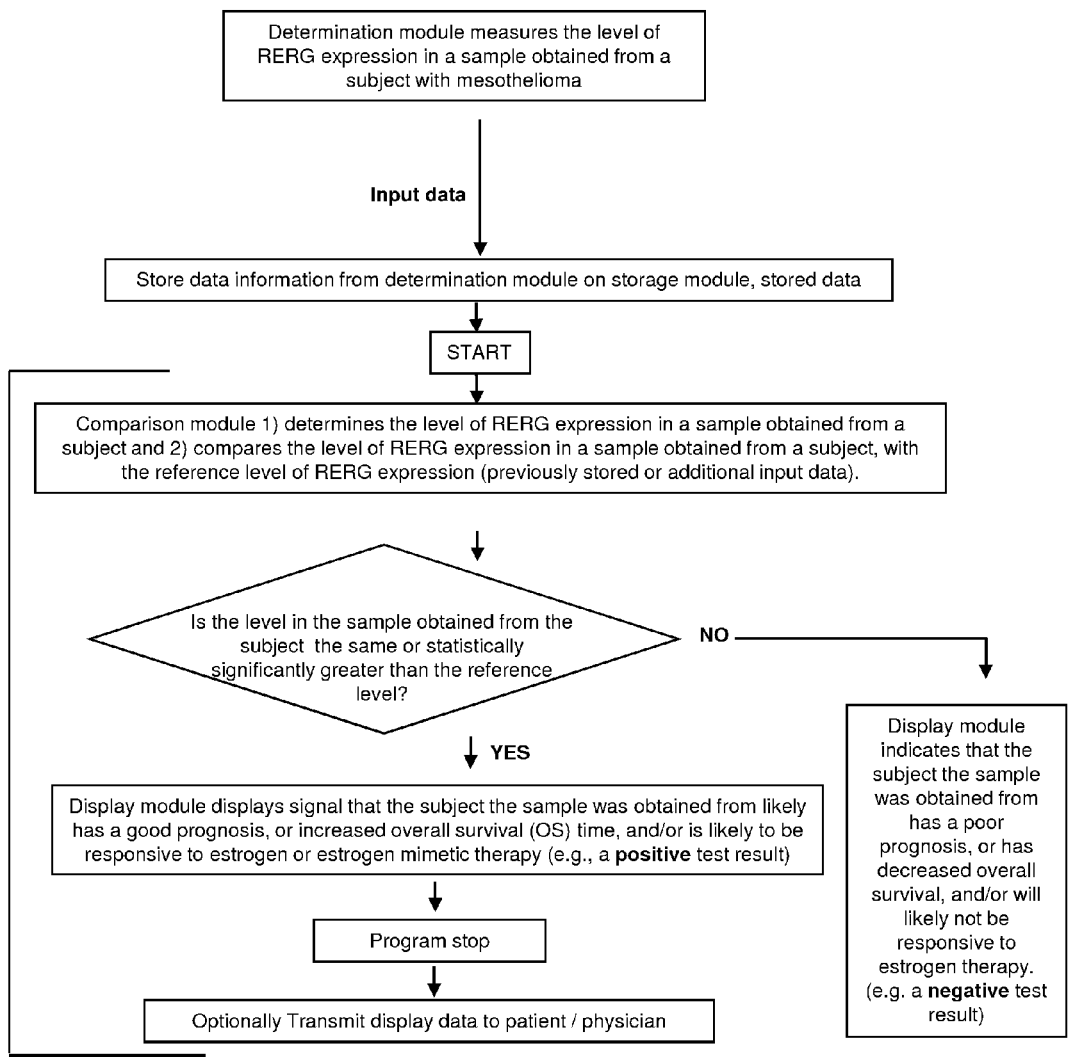
FIG. 10 is a diagram of an exemplary embodiment of a comparison module as described herein.

The "computing module" can use a variety of available software programs and formats for computing the level of RERG expression. Such algorithms are well established in the art. A skilled artisan is readily able to determine the appropriate algorithms based on the size and quality of the sample and type of data. The data analysis tools and equations described herein can be implemented in the computing module of the invention. In some embodiments, the computing module can comprise a computer and/or a computer system. In one embodiment, the computing module further comprises a comparison module, which compares the level of RERG expression in a sample obtained from a subject as described herein with a reference level as described herein (see, e.g. FIG. 10). By way of an example, when the level of RERG expression in a sample obtained from a subject is measured, a comparison module can compare or match the output data with the mean level of RERG expression in a population of mesothelioma subjects classified as having a good prognosis (i.e. a reference level). In certain embodiments, the mean level of RERG expression in a population of mesothelioma subjects identified as having a good prognosis and/or increased overall survival time can be pre-stored in the storage module. During the comparison or matching process, the comparison module can determine whether the level of expression of RERG in the biological sample obtained from a subject is the same as, or statistically significantly greater than the reference level. In various embodiments, the comparison module can be configured using existing commercially-available or freely-available software for comparison purpose, and may be optimized for particular data comparisons that are conducted.

Figure 11:
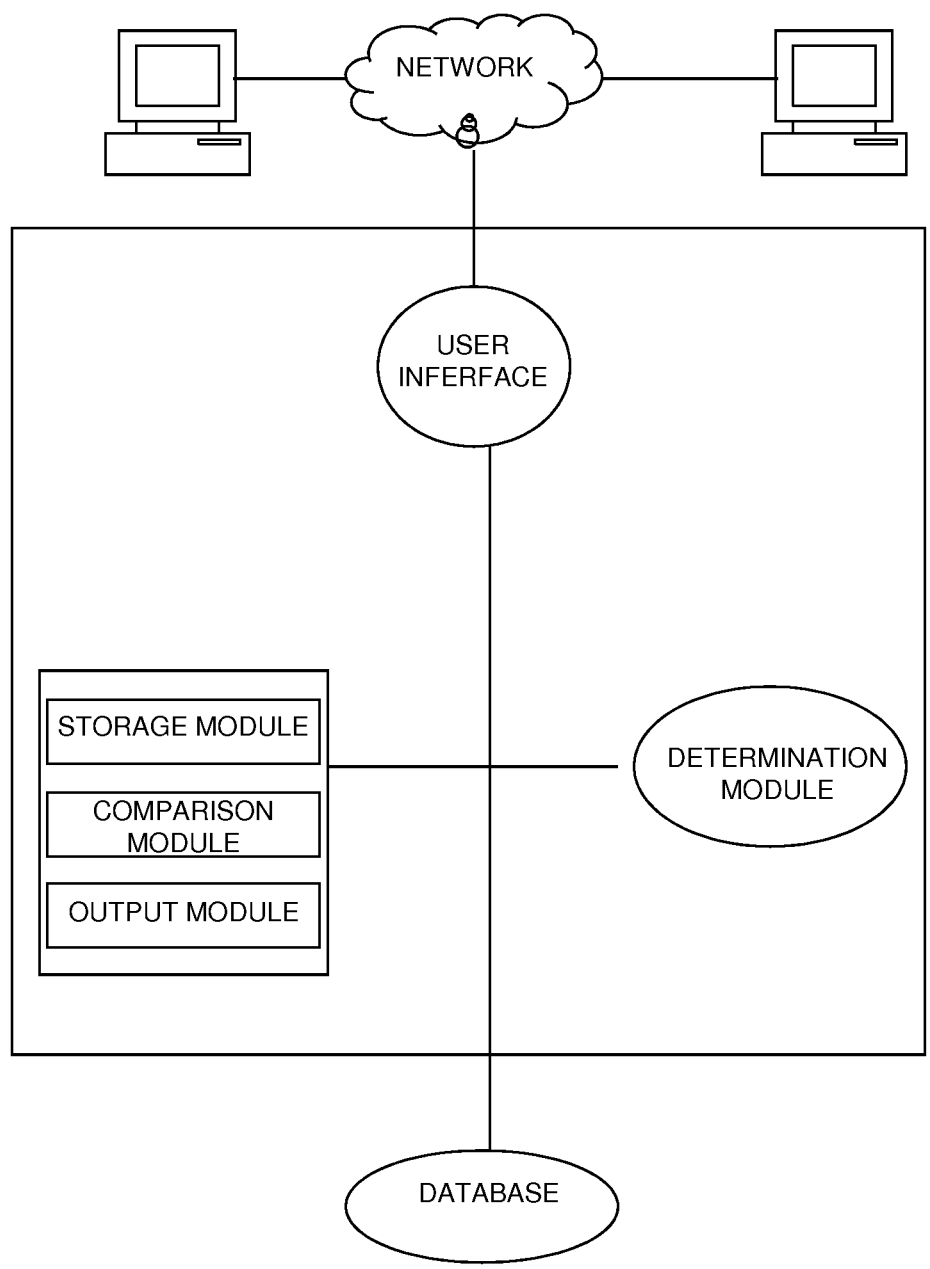
FIG. 11 is a diagram of an exemplary embodiment of an operating system and instructions for a computing system as described herein.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). In some embodiments users can directly access data (via Hypertext links for example) residing on Internet databases using a HTML interface provided by Web browsers and Web servers (FIG. 11).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be a report, e.g. the level of RERG expression (e.g., protein and/or mRNA levels) in the sample obtained from a subject. In some embodiments, a report can denote the level of RERG expression. In some embodiments, the report can denote raw values of the number/level of RERG expression in the test biological sample (plus, optionally, the number/level RERG expression in a reference sample) or it indicates a percentage or fold increase (or fold change) in RERG expression (protein and/or mRNA levels) as compared to the reference RERG expression level, and/or provides a signal that the subject has increased probability of good prognosis and/or increased survival time with mesothelioma.

In some embodiments, if the computing module determines that the level RERG expression in the sample obtained from a subject is the same as, or greater by a statistically significant amount than the reference RERG expression level, the display module provides a report displaying a signal indicating that the level in the sample obtained from a subject is the same as or greater than that of the reference level. In some embodiments, the content displayed on the display module or report can be the relative level of RERG expression in the sample obtained from a subject as compared to the reference level. In some embodiments, the signal can indicate the degree to which the level RERG expression in the sample obtained from the subject varies from the reference level. In some embodiments, the signal can indicate that the subject has an increased probability of a good prognosis and/or increased overall survival time and/or improved survival time with mesothelioma. In some embodiments, the signal can indicate the subject can benefit from treatment with an estrogen therapy, e.g., an estrogen or estrogen mimetic according to the methods as described herein.

In some embodiments, the signal can indicate the degree to which the level RERG expression in the sample obtained from the subject varies from the reference level. In some embodiments, the signal can indicate that the subject has an increased probability of a poor prognosis and/or decreased overall survival time and/or improved survival time with mesothelioma. In such embodiments, the signal can indicate the subject would not be responsive to estrogen therapy and thus may be amenable to treatment with a non-estrogen therapy.

In some embodiments, the content displayed on the display module or report can be a numerical value indicating one of these risks or probabilities. In such embodiments, the probability can be expressed in percentages or a fraction. For example, higher percentage or a fraction closer to 1 indicates the increased probability of a good prognosis and/or increased overall survival time, and/or the subject is likely to be responsive to estrogen therapy. Alternatively, for example, a lower percentage or a fraction closer to 0 indicates the increased probability of a poor prognosis and/or decreased overall survival time, and/or the subject is unlikely to be responsive to estrogen therapy. In some embodiments, the content displayed on the display module or report can be single word or phrases to qualitatively indicate a risk or probability. For example, a word "good" can be used to indicate a high probability of a good prognosis and/or increased overall survival time with mesothelioma, while "poor" can be used to indicate a increased probability of a poor prognosis, and/or decreased overall survival time, and/or likely to be non-responsive to estrogen therapy.

In one embodiment of the invention, the content based on the computing and/or comparison result is displayed on a computer monitor. In one embodiment of the invention, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules of the invention can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

In some embodiments, the system further comprises a means of inputting a value for the level of RERG expression obtained from a subject or a reference value. By way of non-limiting example, the level of zinc can be determined by the determination module of the system. The level of RERG expression can be entered into the computing module of the system. In some embodiments, the inputting means comprises a keyboard or touchscreen which allows a user to type a value which is accepted by the computing module.

Systems and computer readable media described herein are merely illustrative embodiments of the invention for determining the level of RERG expression in a sample obtained from a mesothelioma subject, and therefore are not intended to limit the scope of the invention. Variations of the systems and computer readable media described herein are possible and are intended to fall within the scope of the invention. The modules of the machine, or those used in the computer readable medium, may assume numerous configurations. For example, function may be provided on a single machine or distributed over multiple machines.

A method of diagnosis is also provided. The method comprises detecting the levels of RERG expression protein or nucleic acids in a biological sample. The sample may be derived from a patient. Diagnosis of a cancer state, and its histological type, in a patient may allow for prognosis and selection of therapeutic strategy. Further, the developmental stage of cells may be classified by determining temporarily expressed cancer-associated nucleic acids.

In situ hybridization of labeled probes to tissue arrays may be performed. When comparing the fingerprints between an individual and a standard, the skilled artisan can make a diagnosis, a prognosis, or a prediction based on the findings. It is further understood that the genes that indicate the diagnosis may differ from those which indicate the prognosis and molecular profiling of the condition of the cells may lead to distinctions between responsive or refractory conditions or may be predictive of outcomes.

Kits

In some embodiments, described herein is a kit comprising at least affinity binding molecule which binds a RERG protein and/or RERG gene product (e.g., mRNA) one comprising a detectable label. In some embodiments, the detectable label can be detected by indirect or direct methods. In some embodiments, the affinity binding molecule is an protein binding molecule, e.g., but not limited to an antibody or an antibody fragment or a protein comprising an antigen-binding domain of an antibody. In some embodiments, the affinity binding molecule is a nucleic acid binding probe which binds RERG mRNA. In some embodiments, at least one affinity-binding molecule can be immobilized on a solid support. In some embodiments, a kit can further comprise reagents for generating and/or detecting a signal from a detectable label.

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be used for the amplification, detection, identification or quantification of a target nucleic acid sequence. The kit may comprise a poly(T) primer, a forward primer, a reverse primer, and a probe.

Any of the compositions described herein may be comprised in a kit. In a non-limiting example, reagents for isolating RERG mRNA, labeling mRNA, and/or evaluating RERG mRNA expression levels using an array are included in a kit. The kit may further include reagents for creating or synthesizing miRNA probes. The kits will thus comprise, in suitable container means, an enzyme for labeling the RERG mRNA by incorporating labeled nucleotide or unlabeled nucleotides that are subsequently labeled. It may also include one or more buffers, such as reaction buffer, labeling buffer, washing buffer, or a hybridization buffer, compounds for preparing the RERG mRNA probes, components for in situ hybridization and components for isolating RERG mRNA. Other kits of the invention may include components for making a nucleic acid array comprising a target probe for RERG mRNA, and thus, may include, for example, a solid support.

In some embodiments of the present invention may be defined in any of the following numbered paragraphs:

1. A method of treating a subject with mesothelioma, comprising administering a composition comprising an effective amount of an estrogen or an estrogen mimetic to the subject if a biological sample from the subject has been determined to have an expression of the Ras-like, estrogen-regulated, growth inhibitor (RERG) protein or the RERG gene product at the same level or above a reference level for the RERG protein or gene product.

2. The method of paragraph 1, wherein the mesothelioma is malignant mesothelioma.

3. The method of paragraph 2, wherein the malignant mesothelioma is malignant plural mesothelioma (MPM).

4. The method of paragraph 1, further comprising selecting the subject to be treated before onset of said administering, comprising assaying a biological sample from the subject for the expression of the Ras-like, estrogen-regulated, growth inhibitor (RERG) protein or the RERG gene product, and selecting the subject where the expression of the RERG protein or gene product is at the same level or above a reference level for RERG protein or gene product.

5. The method of paragraph 1, wherein the estrogen mimetic is an estrogen-like agent which has a similar biological function to estrogen.

6. The method of paragraph 1, wherein the estrogen is a natural or synthetic estrogen.

7. The method of paragraph 1, wherein the estrogen is selected from the group consisting of estradiol, estrone, estriol, 17α-estradiol, 17β-estradiol.

8. The method of paragraph 1, wherein the estrogen mimetic is selected from the group consisting of: 2-fluoro-3,17β-estradiol, 2,4-difluoro-3,17β-estradiol, 2-fluoroestrone, 2,4-difluoroestrone, 2-fluoro-17α-ethinyl-3,17β.-estradiol, 2,4-difluoro-17α-ethinyl-3,17β-estradiol, 2-fluoro-17α-ethinylestradiol 3-methyl ether, 2,4-difluoro-17α-ethinylestradiol 3-methyl ether, 15.βH,3'H-cycloprop[14,15]-estra-1,3,5(10),8-tetraen-3,17α-diol, 5.βH,3'H-cycloprop[14,15]-18α-homoestra-1,3,5(10),8-tetraen-3, 17α-diol, 17α-hydroxy-15βH,3'H-cycloprop[14,15]-estra-1,3,5(10),8-tetraen-3-yl-pentanoate, 17-methylene-15βH, 3'H-cycloprop[14,15]-estra-1,3,5(10),8-tetraen-3-ol, 15αH, 3'H-3',3'-difluorocycloprop[14,15]-estra-1,3,5(10),8-tetraen-3,17α-diol, 17-methylene-15βH,3'H-cycloprop[14, 15]-estra-1,3,5(10),8-tetraen-3-yl-sulfamate, 17-difluoromethylene-15βH,3'H-cycloprop[14,15]-estra-1, 3,5(10),8-tetra en-3-ol, 3-methoxy-15β-methyl-3'H-cycloprop[14,15]-estra-1,3,5(10),8-tetraen-3-ol, 15α-methyl-3'H-cycloprop[14,15]-estra-1,3,5(10),8-tetraen-3,17α-diol, 17-difluoromethylene-15βH,3'H-cycloprop[14,15]-estra-1, 3,5(10),8-tetra en-3-yl-(tetramethylenimino)sulfonate and 17-methylene-3'H-cycloprop[8,9]-15.beta.H,3'H-cycloprop [14,15]-estra-1,3,5(10)-trien-3-ol;

9. The method of paragraph 1 or 4, wherein the biological sample comprises a biopsy sample, blood sample, plasma sample, urine sample.

10. The method of paragraph 8, wherein the biopsy is a surgical biopsy.

11. The method of paragraph 9, wherein the biopsy sample is a fine needle aspiration (FNA).

12. The method of paragraph 1, wherein the subject is male or female.

13. The method of paragraph 11, wherein the subject has had prior exposure to asbestos.

14. The method of paragraph 11, wherein the subject has no known prior exposure to asbestos.

15. The method of any of paragraphs 1 to 13, further comprising administering an additional therapeutic agent to the subject.

16. The method of paragraph 11, wherein the additional therapeutic agent is a chemotherapeutic agent or an agent used to treat mesothelioma.

17. The method of paragraph 12, wherein an agent used to treat mesothelioma is selected from the group consisting of pemetrexed, cisplatin and carboplatin.

18. An assay comprising: (a) contacting a biological sample from a subject with an affinity binding molecule which binds to the Ras-like, estrogen-regulated, growth inhibitor (RERG) protein or the RERG gene product; (b) measuring the amount of affinity binding molecule which is bound to the RERG protein or RERG gene product; wherein a level of the affinity binding molecule which is bound to the RERG protein or RERG gene product at the same level or above a reference level indicates the subject has an increased probability of good prognosis and improved survival time after diagnosis of mesothelioma, and wherein a level of the affinity binding molecule which is bound to the RERG protein below the reference level indicates the subject has an increased probability of a poor prognosis and decreased survival time after diagnosis with mesothelioma.

19. An assay comprising: (a) measuring or quantifying the amount of Ras-like, estrogen-regulated, growth inhibitor (RERG) protein or gene expression product in a biological subject obtained from the subject, (b) comparing the measured or quantified amount of RERG protein or gene expression product with a reference value, (c) identifying the subject as having an increased probability of a good prognosis and improved survival time if the amount of RERG protein or gene expression product is the same as, or increased relative to the reference value, and identifying the subject has having an increased probability of a poor prognosis and decreased survival time if the amount of RERG protein or gene expression product is decreased relative to the reference value.

20. An assay comprising: (a) contacting a biological sample from a subject with at least one RERG specific antibody or at least one RERG specific probe; wherein the RERG specific antibody or RERG probe comprises a detectable label or means of generating a detectable signal, (b) detecting the presence or intensity of a detectable signal associated with RERG specific antibody or RERG probe; wherein an increased, or same level of RERG protein or RERG gene product, as indicated by the detectable signals, relative to a reference level indicates the subject has a probability of a good prognosis and improved survival time after diagnosis of mesothelioma, and wherein a decreased level of RERG protein or gene expression product as indicated by the detectable signals, relative to a reference level, indicates an increased probability of a poor prognosis and decreased survival time after diagnosis with mesothelioma.

21. An assay to determine if a subject with mesothelioma will benefit from treatment with an estrogen therapy, the assay comprising: (a) contacting a biological sample obtained from the subject with at least one an affinity binding molecule which binds to the Ras-like, estrogen-regulated, growth inhibitor (RERG) protein or the RERG gene product; (b) measuring the amount of affinity binding molecule which is bound to the RERG protein or RERG gene product; wherein an increased, or same level of RERG protein or RERG gene product relative to a reference level indicates the subject will benefit from treatment with estrogen therapy.

22. The assays of any of paragraphs 18 to 21, wherein the affinity-binding molecule is a RERG specific antibody or RERG probe.

23. The assays of paragraph 22, wherein the RERG specific antibody or RERG probe comprises a detectable label or means of generating a detectable signal.

24. The assays of any of paragraphs 18 to 23, wherein the affinity binding molecule is attached to a support.

25. The assay of paragraph 24, wherein the level of RERG gene product is measured or quantified by RT-PCR.

26. The assays of any of paragraphs 18 to 24, wherein the level of RERG protein is measured by or quantified by measuring the binding of a protein-binding molecule.

27. The assay of paragraph 26, wherein the protein-binding molecule is an antibody or antibody fragment which specifically binds to the RERG protein.

28. A computer system for determining if a subject with mesothelioma has a probability of a good prognosis or improved survival time, the system comprising: (a) a measuring module configured to measure the level of the RERG protein and/or RERG gene product in a biological subject obtained from a subject; (b) a storage module configured to store output data from the measuring module; (c) a comparison module adapted to compare the data stored on the storage module with a reference level, and to provide a retrieved content, and (d) a display module for displaying whether the level of RERG protein and/or RERG gene product in a biological sample obtained from a subject is the same as, or greater, by a statistically significant amount, than the reference level and/or displaying the relative levels RERG protein and/or RERG gene product in the biological sample.

29. The system of paragraph 28, wherein the measuring module measures the presence or intensity of a detectable signal from an affinity-binding molecule which binds to the Ras-like, estrogen-regulated, growth inhibitor (RERG) protein or the RERG gene product, wherein the affinity-binding molecule comprises a detectable label or means of generating a detectable signal.

30. The system of paragraph 29, wherein the affinity binding molecule is a protein-binding molecule.
31. The system of paragraph 30, wherein the measuring module measures the presence or intensity of a detectable signal from an affinity-binding molecule from an immunoassay indicating the level of RERG protein present in the biological sample.
32. The system of any of paragraphs 29 to 31, wherein if the computing module determines that the level of RERG protein or RERG gene product in the biological sample obtained from a subject is the same as, or greater by a statistically significant amount than the reference level, the display module displays a positive signal indicating that the level in the sample obtained from a subject is greater than that of the reference level.
33. The system of paragraphs 32, wherein the signal indicates that the subject has a good prognosis and/or increased survival time as compared to a subject who has the level of RERG protein or RERG gene product below a reference level.
34. The system of any of paragraphs 29 to 31, wherein if the computing module determines that the level of RERG protein or RERG gene product in the biological sample obtained from a subject is below by a statistically significant amount than the reference level, the display module displays a negative signal indicating that the level in the sample obtained from a subject is lower than that of the reference level.
35. The system of paragraphs 34, wherein the signal indicates that the subject has a poor prognosis and/or decreased survival time as compared to a subject who has the level of RERG protein or RERG gene product at the same level, or above a reference level.
36. The system of any of paragraphs 29 to 33, wherein the signal indicates the subject can benefit from treatment with estrogen or an estrogen mimetic.
37. The system of any of paragraphs 29 to 36, wherein the signal indicates the level of RERG protein or RERG gene product in the biological sample obtained from a subject as compared to the reference level, or a degree of difference of level of RERG protein or RERG gene product as compared to the reference level.
38. The assay of any of paragraphs 29 to 37, wherein the affinity-binding molecule is a protein-binding molecule or a nucleic-acid binding molecule.
39. The system of any of paragraphs 29 to 38, wherein the biological sample comprises a biological tissue selected from the group consisting of: whole blood; peripheral blood; whole peripheral blood; biopsy sample, plasma sample; and products thereof.
40. The system of any of paragraphs 29 to 39, wherein the level of RERG protein is measured by immunocytological methods.
41. The system of any of paragraphs 29 to 40, wherein the affinity-binding molecule comprises an antibody or a polypeptide comprising an antigen-binding domain of an antibody.
42. The system of any of paragraphs 29 to 41, wherein the level of RERG gene product is measured by RT-PCR methods.
43. The system of any of paragraphs 29 to 42, wherein the affinity-binding molecule comprises a probe which can bind the RERG gene product.
44. The system of any of paragraphs 29 to 42, wherein the subject is a human.
45. The system of any of paragraphs 29 to 44, further comprising creating a report based on the level of RERG protein or RERG gene product in the biological sample.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

EXAMPLES

Malignant pleural mesothelioma (MPM) is a highly lethal cancer, and a approximately 2,500 new cases of MPM in the US annually. MPM is largely thought of as a disease of men, resulting primarily from occupational exposure to asbestos, however, women were usually exposed in a second hand manner from the men.

Female gender is a positive prognostic factor for malignant pleural mesothelioma (MPM). Although women represent a smaller fraction of MPM patients, they represent a disproportionately high number of the long-term survivors (Wolf et al. Ann Thorac Surg 2010). The female gender is associated with overall improved prognosis and increased overall survival with MPM. Female gender is associated with improved prognosis using the CALGB and EORTC scoring systems. In a study of 3-year survival in 636 patients with EPP, the inventors discovered that the longest survival was experience by women under the median age of 56 years (Sugarbaker et al. European Journal of Cardio-Thoracic Surgery 2011). In addition, at least one prior study has reported ESR-Beta protein levels associated with improved survival improved survival in mesothelioma (Pinton G. et al, Cancer Res. 2009).

However there has been limited study of estrogen or estrogen-regulated genes in association with mesothelioma outcome. Previously, the inventors have developed a four-gene expression ratio-based algorithm for MPM outcome prediction which can be used as a tool in the discovery of biomarkers critical to prognosis (De Rienzo et al., Clin Cancer Res, 2011, 17 (2), 310-316). In particular, the inventors have previously demonstrated, using microarray analysis and a gene ratio based algorithm (TM4SF1/PKM2)×(TM4SF1/ARHGDIA)×(COBLL1/ARHGDIA), that several biomarkers are useful to predict the survival of a subject with MPM after surgery. These biomarkers have been validated using both retrospective and Prospective Validation (Gordon et al. J Natl Cancer Inst (2003) 95:598; Gordon et al. Clin Cancer Res (2005) 11:4406, and Gordon et al. J Natl Cancer Inst (2009) 101:678). Accordingly, the inventors used these predictive gene ratio test for classification of samples by predicted outcome and in terms of overall survival (OS).

Example 1

Herein the inventors have applied the ratio test to expression profiling data from 39 MPM samples analyzed by Illumina microarray and 48 MPM samples analyzed by Codelink microarray, to divide the samples into predicted good and poor outcome groups. Next, the expression of candidate estrogen-regulated genes was evaluated for each microarray sample to identify significantly differentially expressed genes. In addition, MPM microarray samples were divided based on expression of these identified genes to evaluate associations with survival.

One gene, Ras-like, estrogen-regulated, growth inhibitor (RERG) was significantly differentially expressed between good and poor outcome samples in both microarrays ($p<0.0001$). Validation of these results, on a subset of the MPM samples, by quantitative real-time PCR (qRT-PCR) demonstrated that RERG was more highly expressed in good than poor outcome samples ($p=0.034$). When epithelial MPM microarray samples were divided by RERG expression, there was a significant difference in survival between the three upper quartiles and the lower quartile samples in both microarray platforms ($p<0.001$).

Experimental methods: Mesothelioma tumor samples were analyzed by microarray, and using the predictive test the microarray samples were classified into two groups; (i) predicted good outcome and (ii) predicted poor outcome. Individual genes expression was determined in each outcome group using microarray analysis. Genes differentially expressed between outcome groups but not in the predictive gene ratio test were identified.

Figure 2:
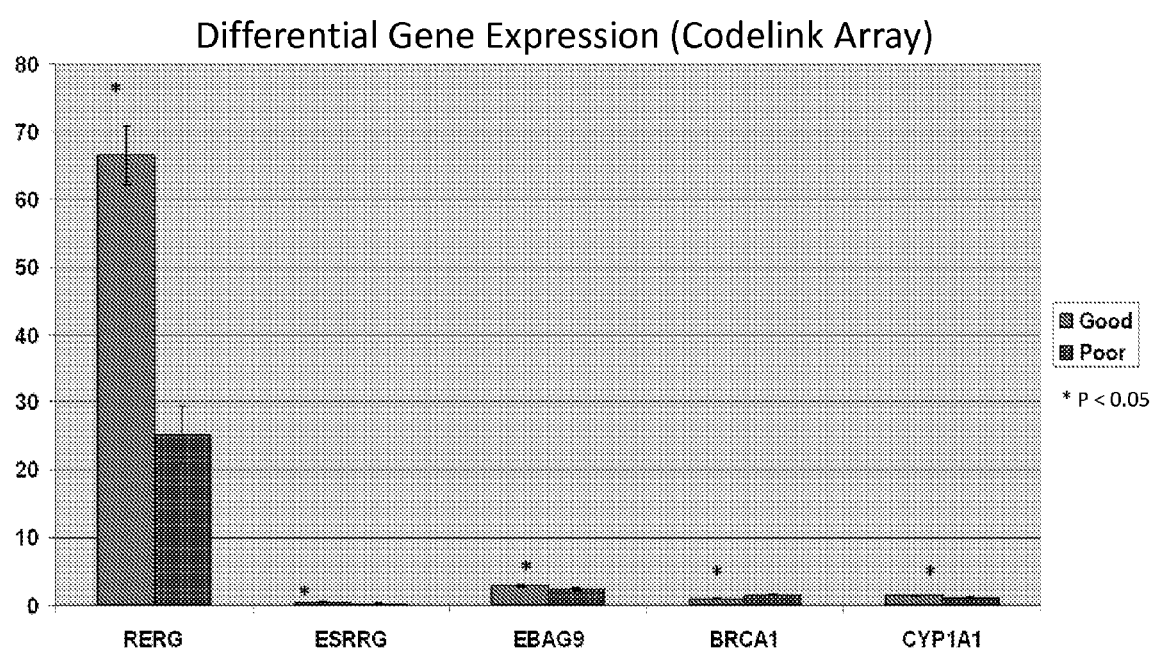
FIG. 2 is a histogram of the differentially expressed candidate estrogen-regulated genes in 48 samples assessed by Codelink array showing that RERG is significantly differentially expressed in samples from mesothelioma subjects predicted to have a good prognosis or bad prognosis. RERG was demonstrated to be at least about 3-fold greater in samples from mesothelioma subjects predicted to have a good outcome as compared to mesothelioma subjects predicted to have a poor outcome.
Figure 3:
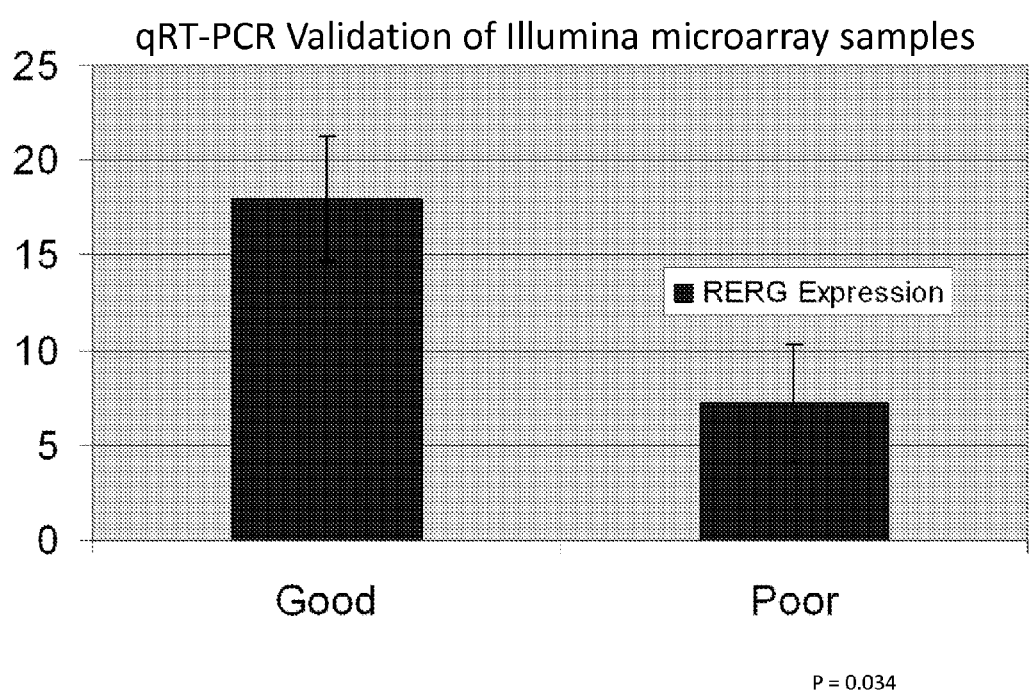
FIG. 3 shows a histogram of RERG expression in 40 samples from mesothelioma subjects predicted to have a good or bad survival outcome. RERG mRNA expression in tumor biopsy samples, e.g., lung biopsy samples was determined to be at least 2-fold increased in subjects having a good survival outcome as compared to subjects with a poor outcome.

Results: The inventors investigated genes differentially regulated genes in mesothelioma subjects predicted to have a good and poor overall survival prognosis. Several candidate estrogen-regulated genes were identified to be differentially expressed between the good and bad outcome groups (FIG. 1) in 40 mesothelioma samples assessed, as detected by illumina array. These genes include CTP1B1, BCAR1, ERCC1, RERG, ESRRG and ESRRB. This was confirmed by Codelink Array (FIG. 2) in the analysis of 48 mesothelioma samples, which demonstrated that RERG was the most differentially expressed of the genes analyzed (FIG. 2). To validate the microarray analysis, gene expression was measured in the same 40 mesothelioma samples by real time PCR (FIG. 3).

RERG was confirmed to be differentially regulated between mesothelioma samples categorized as good and poor outcome. RERG (Ras-like, estrogen regulated, growth inhibitor) is a member of the RAS superfamily of GTPases, and inhibits cell proliferation and tumor cell formation. Overexpression of RERG has been reported to be associated with inhibition of breast tumor cell growth (Finlin et al, J. Biol Chem 2001; 347 (Pt 1): 223-231; Sorlie et al, PNAS 2001, 98 (19): 10869-10874). Additionally, high RERG expression has been reported to be associated with longer survival in ER+ luminal-like breast cancer (Habashy et al. Breast Cancer Res Treat 2011) and strong RERG expression has been reported to be associated with longer relapse free survival in ER+/PR+ breast cancers treated with adjuvant tamoxifen (Kerr and Wittliff. Horm Canc 2011).

Example 2

Figure 4:
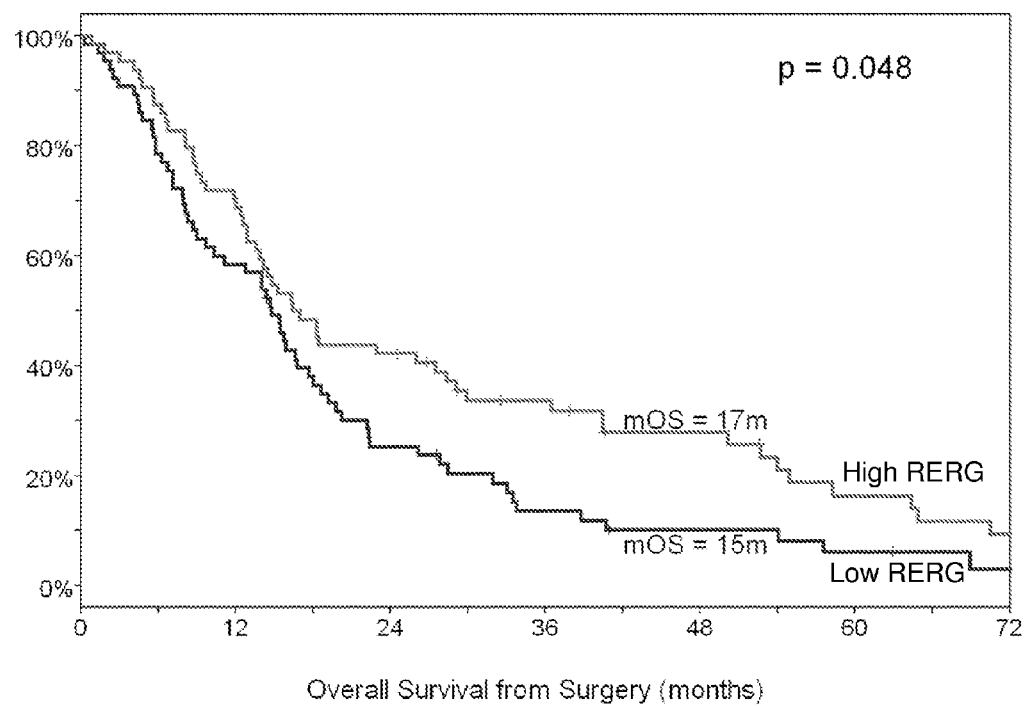
FIG. 4 shows the levels of RERG expression on the overall survival of mesothelioma subjects. RERG expression was measured in 128 epithelial MPM cases by Affymetrix® Human Gene 1.1 ST Array. Subjects with increased RERG expression levels had a mean overall survival (mOS) of 17 months as compared to subjects with low RERG expression, which had a mOS of 15 months.
Figure 5:
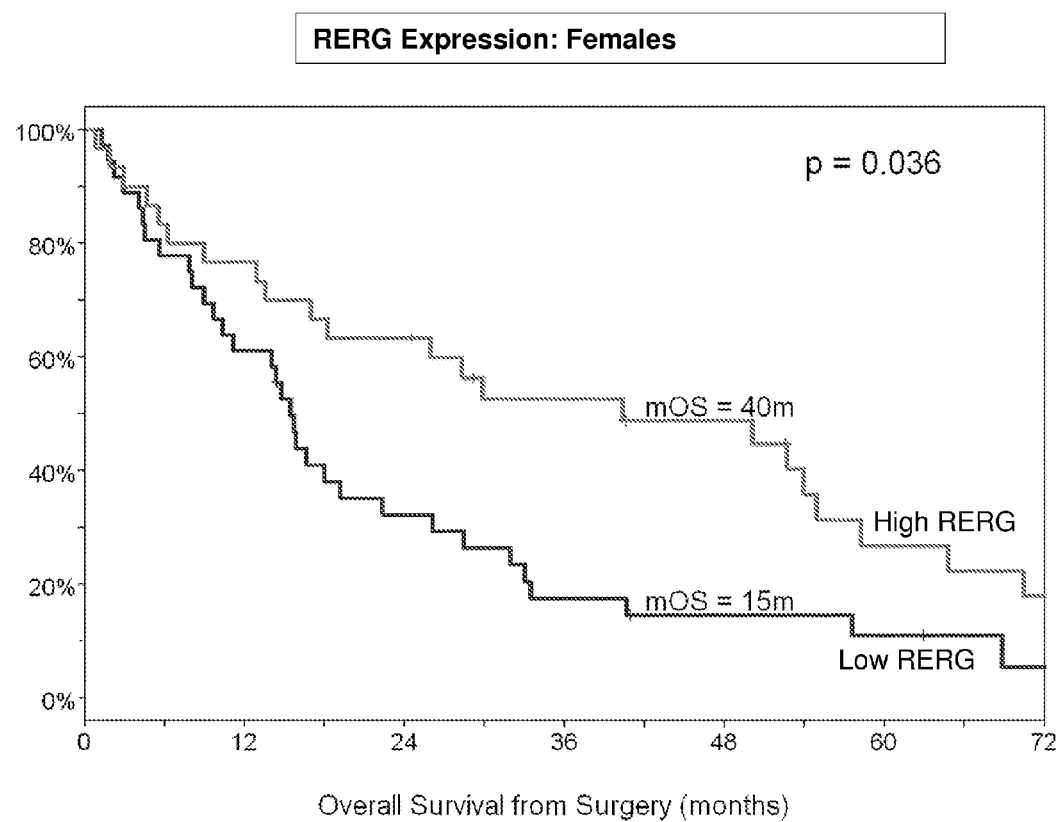
FIG. 5 shows the levels of RERG expression on the overall survival of female mesothelioma subjects. Female mesothelioma subjects with increased RERG expression levels had a mean overall survival (mOS) of 40 months as compared to female subjects with low RERG expression, which had a mOS of 15 months, demonstrating that RERG expression in female subjects increased the median survival or longevity of female subjects by about 25 months.
Figure 6:
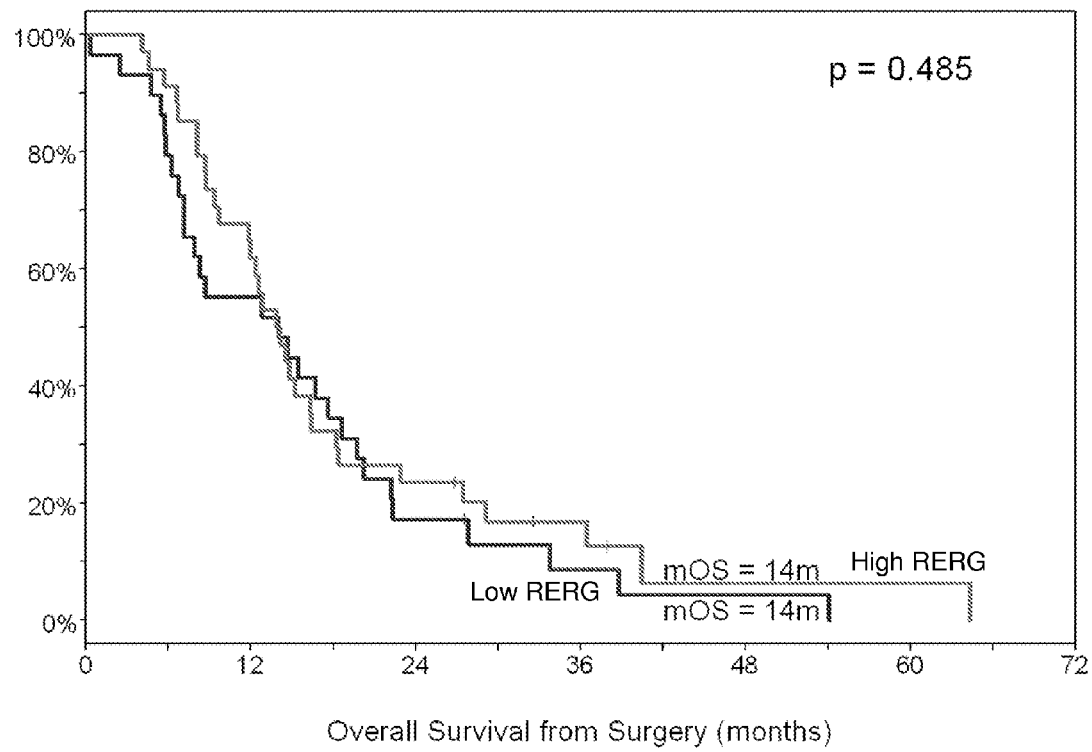
FIG. 6 shows the levels of RERG expression on the overall survival of male mesothelioma. Male mesothelioma subjects with increased RERG expression levels had a mean overall survival (mOS) of 14 months, which is similar to male subjects with low RERG expression.
Figure 7:
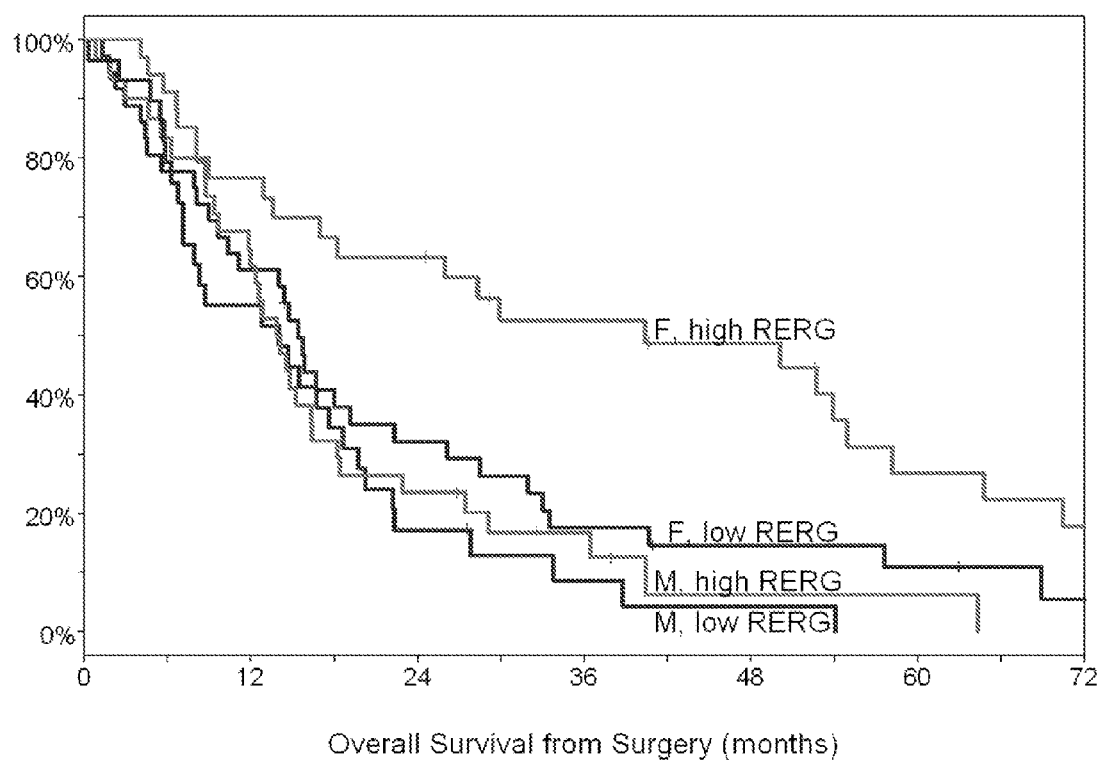
FIG. 7 shows the levels of RERG expression by gender on the overall survival of male and female mesothelioma subjects. Only female mesothelioma subjects with increased RERG expression levels have a survival advantage and increased median overall survival as compared to female subjects with low RERG expression or male mesothelioma subjects with high or low RERG expression. $p=0.036$ for female low RERG vs. female high RERG, and $p=0.170$ for female low RERG vs. male low RERG, $p=0.431$ for female low RERG vs. male, high RERG.
Figure 8:
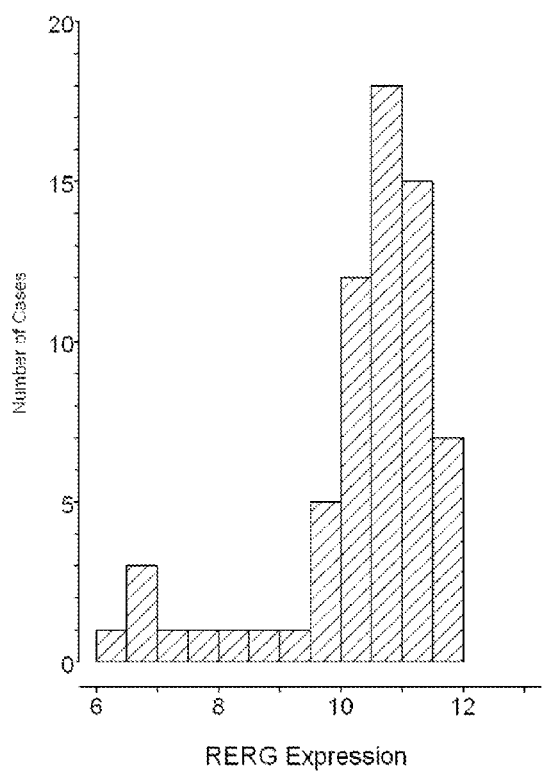
FIG. 8 shows a histogram of the distribution of RERG expression in different genders. The distribution of mesothelioma subjects with high and low expression of RERG is the same in both genders. There is no difference of the distribution of RERG expression by gender ($p=0.658$).
Figure 8:
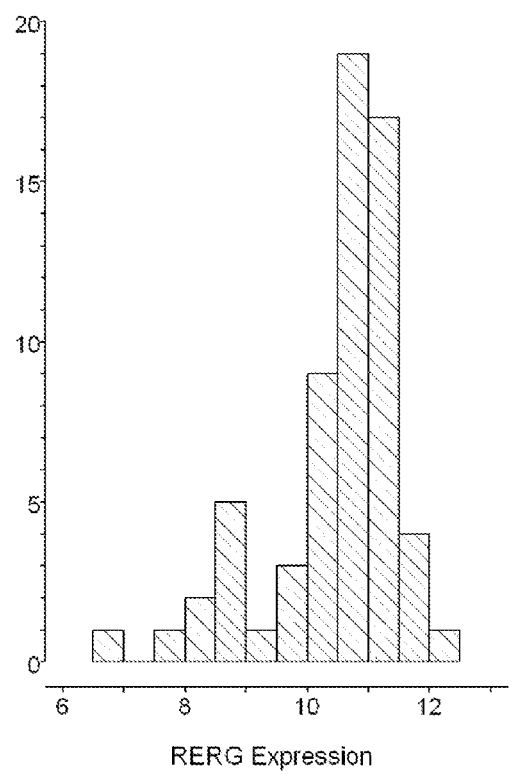

The inventors investigated the level of RERG expression in mesothelioma subjects predicted to have a good and poor overall survival prognosis. 128 epithelial MPM cases were assessed and male and female pairs were matched by age and nodal status. RERG expression measured by AFFYMETRIX® Human Gene 1.1 ST Array Plate high-throughput expression profiling system. The inventors assessed the RERG expression with overall survival discovered that increased RERG expression conferred a survival benefit and increased the median overall survival (mOS) after surgery by at least 2 months (FIG. 4). Surprisingly, the inventors discovered that increased expression of RERG in female subjects was associated with an increase in the overall survival (FIG. 5), and determined that RERG expression increased the median overall survival (mOS) in females by at about 25 months from about 15 months to about 40 months. However, in contrast, the inventors surprisingly discovered that increased RERG expression in male mesothelioma subjects did not have an increased in overall survival (OS) (FIG. 6).

Accordingly, the inventors have uses a predictive gene expression ratio test to successfully identify genes differentially expressed in good and poor outcome groups, and identified estrogen-regulated genes associated with outcome, in particular RERG expression was discovered to be associated with greater overall survival in female mesothelioma patients, but not in male subjects, however, male and female subjects could be selected based on a high level of RERG expression to be candidates for estrogen therapy (e.g., administered an estrogen or estrogen mimetic) for the treatment of mesothelioma.

Accordingly, herein the inventors demonstrate that RERG mediates survival benefit in MPM, and subjects with MPM have increased survival time upon diagnosis of mesothelioma as compared to subjects who do not have high expression of RERG. As RERG is likely activated by estrogen, subjects with MPM which have high levels of RERG above a threshold level are amenable and can be treated with estrogen or an estrogen-like molecule, e.g., an estrogen mimetic or molecule which enhances estrogen levels.

REFERENCES

The references are incorporated herein in their entirety by reference.

```
SEQ LISTING:
Ref Seq: NM_32918.2
RERG (isoform 1)
                                                             SEQ ID NO: 1
   1 actgcagcat cctggccgct gagcgcagcg gccttggccg ggctcagctc gcgtcctgcc 61 gcagtccctc cgccgctagt cggagcgagc gcgagtgagg agaccccgc cgggccactg 121 gcacttgctt ctgcggcgag tcccacccac gaccgcagcc cagcaactcg caaacgcaac 181 ctgaagcctg gctgcgcag tgtgggaggg cttcgcgatc ttgggggacc cattccgaac 241 ttgcagagga ccgtagctct cctggcctgg agagtgtgaa caggattgtg gactcttcca 301 agattcacaa tgatatggtg aatccaaaga ctggaaccaa aaagatttac tcagtgcttt 361 agttttaaca acagtaaatt gtctaccaac acccatcatg gctaaaagtg cggaggtcaa 421 actggcaata tttgggagag caggcgtggg caagtcagct cttgtagtga gatttctgac 481 caaacggttc atctgggaat atgatcccac cctcgaatca acctaccgac accaagcaac 541 catcgatgat gaagttgttt ccatggagat actagacact gctggtcagg aagataccat 601 tcagagggag gggcacatgc gatggggga aggctttgtg ctggtctacg acattactga 661 ccgaggaagt tttgaggaag tgctgccact taagaacatc ctagatgaga tcaaaaagcc 721 caagaatgtg actctcatct tggttggaaa caaagctgac ttggaccact ccaggcaggt 781 tagcacagaa gaaggagaga agctggccac agaattggct tgtgcttttt acgagtgctc 841 tgcctgcact ggagaaggga acatcacaga gatattctat gaattgtgtc gagaggtgcg 901 tcgccggagg atggtgcagg gcaagacgag gcgacgcagc tccaccacgc atgtcaagca 961 agccattaac aagatgctca ccaaaatcag tagttaggca gcccagctga ggtggaccaa 1021 ctaattggaa acactcttcc ccttctgttc ccctttcaaa aataaaacaa atatttgcat 1081 tctttgtttg gattctgaga aatgtctggg cttcccattg tttctggcct ctaataggtt 1141 gggaagtttt agcgtgtttt atgcaatttc agtgctaaca atttcttcct ttcctgcttg 1201 aataagatac actctaatgg catttgaaca tgtaatcacc agagattctg aaatgactgg 1261 tttatgttaa gctatttta ggcatcttca ccttgcttta agtaggttga agtttttgca 1321 aaggcattta aaaattcaat ttcttgtcag atactacaaa taattttctt aaaagtctaa 1381 gatagcagaa aatacagtaa aaacacagga gaagaagctg agctattgga acaggaaata 1441 gaaggaactc tagtttctgt ttgaagtgag gattttctga attatctaat atcatctagg 1501 ttttctttaa aattttattt tgttcttcag ttcaagcatc ttctcactaa tgtttttcac 1561 tataacagag aattcatttc aatttgagtt ggttctctca atgatctatt gatcattaca 1621 ccctaactct ccttccttgg ctcaaacaat attttcccta taacaaaggc aataggacac 1681 aaaattcaca tcctgctggg cctttttttca tcaagtcagg gtgatataaa aacattggaa 1741 gtcttttcac caaaccctga ctttattgaa tgctagtaga agatgtagaa ttagagacat 1801 ctgatttgtt tatcaccttta gcagaaaaac cacagtccaa aagacaagca aattaagaat 1861 ggagcttaac catgcctcca ttgggaagtc tagactttga gccaggtaca gtaagaaaaa 1921 ttagcctctg attcattaag tttgccacat gacttatttt gatatttgg atacattaac 1981 tcacttagga gaattcagaa aagaatgggt gattaaagtt cattacagct gaataaatgt 2041 gtctaaaaca gactcttgta ttctgaaagt acagtctaca actgataaaa ccttatgatt 2101 cttttctccc ccattatgcc cctatatata tcaagatttg ggtactttat tttagtagaa
```

-continued

```
2161 aatatatatc ttttacatat gtatgtattt ataaatgcat agatatatgt ataaaaattt
2221 gtaagcgtta gcggcattaa ttcaccaatg catttggaca acttgatgta actgacttta
2281 ttttatgtga ctataataaa aagcataatt ttctcattct gtcat
```

Ref Seq: NM_001190726.1
RERG (isoform 2)

SEQ ID NO: 2

```
   1 actgcagcat cctggccgct gagcgcagcg gccttggccg ggctcagctc gcgtcctgcc
  61 gcagtccctc cgccgctagt cggagcgagc gcgagtgagg agaccccgc cgggccactg
 121 gcacttgctt ctgcggcgag tcccacccac gaccgcagcc cagcaactcg caaacgcaac
 181 ctgaagcctg ggctgcgcag tgtgggaggg cttcgcgatc ttgggggacc cattccgaac
 241 ttgcagagga ccgtagctct cctggcctgg agagtgtgaa caggattgtg gactcttcca
 301 agattcacaa tgtatggtg aatccaaaga ctggaaccaa aaagatttac tcagtgcttt
 361 agttttaaca acagtaaatt gtctaccaac acccatcatg gctaaaagtg cggaggtcaa
 421 actggcaata tttgggagag caggcgtggg caagtcagaa tcaacctacc gacaccaagc
 481 aaccatcgat gatgaagttg tttccatgga gatactagac actgctggtc aggaagatac
 541 cattcagagg gaggggcaca tgcgatgggg ggaaggcttt gtgctggtct acgacattac
 601 tgaccgagga agttttgagg aagtgctgcc acttaagaac atcctagatg agatcaaaaa
 661 gcccaagaat gtgactctca tcttggttgg aaacaaagct gacttggacc actccaggca
 721 ggttagcaca gaagaaggag agaagctggc cacagaattg gcttgtgctt tttacgagtg
 781 ctctgcctgc actggagaag ggaacatcac agagatattc tatgaattgt gtcgagaggt
 841 gcgtcgccgg aggatggtgc agggcaagac gaggcgacgc agctccacca cgcatgtcaa
 901 gcaagccatt aacaagatgc tcaccaaaat cagtagttag gcagcccagc tgaggtggac
 961 caactaattg gaaacactct tcccttctg ttcccttc aaaataaaa caaatattg
1021 cattctttgt ttggattctg agaaatgtct gggcttccca ttgtttctgg cctctaatag
1081 gttgggaagt tttagcgtgt tttatgcaat ttcagtgcta acaatttctt cctttcctgc
1141 ttgaataaga tacactctaa tggcatttga acatgtaatc accagagatt ctgaaatgac
1201 tggtttatgt taagctattt ttaggcatct tcaccttgct ttaagtaggt tgaagttttt
1261 gcaaaggcat ttaaaaattc aatttcttgt cagatactac aaataatttt cttaaaagtc
1321 taagatagca gaaaatacag taaaaacaca ggagaagaag ctgagctatt ggaacaggaa
1381 atagaaggaa ctctagtttc tgtttgaagt gaggattttc tgaattatct aatatcatct
1441 aggttttctt taaaatttta ttttgttctt cagttcaagc atcttctcac taatgttttt
1501 cactataaca gagaattcat ttcaatttga gttggttctc tcaatgatct attgatcatt
1561 acaccctaac tctccttcct tggctcaaac aatatttttcc ctataacaaa ggcaatagga
1621 cacaaaattc acatcctgct gggccttttt tcatcaagtc agggtgatat aaaaacattg
1681 gaagtctttt caccaaaccc tgactttatt gaatgctagt agaagatgta gaattagaga
1741 catctgattt gtttatcacc ttagcagaaa aaccacagtc caaagacaa gcaaattaag
1801 aatggagctt aaccatgcct ccattgggaa gtctagactt tgagccaggt acagtaagaa
1861 aaattagcct ctgattcatt aagtttgcca catgacttat tttgatattt tggatacatt
1921 aactcactta ggagaattca gaaaagaatg ggtgattaaa gttcattaca gctgaataaa
1981 tgtgtctaaa acagactctt gtattctgaa agtacagtct acaactgata aaaccttatg
2041 attctttct cccccattat gccctatat atatcaagat ttgggtactt tattttagta
2101 gaaaatatat atcttttaca tatgtatgta tttataaatg catagatata tgtataaaaa
```

-continued

```
2161 tttgtaagcg ttagcggcat taattcacca atgcatttgg acaacttgat gtaactgact 2221 ttattttatg tgactataat aaaaagcata attttctcat tctgtcat
```

Ref Seq ID: NP_116307.1
RERG (isoform 1)

SEQ ID NO: 3

```
  1 maksaevkla ifgragvgks alvvrfltkr fiweydptle styrhqatid devvsmeild 61 tagqedtiqr eghmrwgegf vlvyditdrg sfeevlplkn ildeikkpkn vtlilvgnka 121 dldhsrqvst eegeklatel acafyecsac tgegniteif yelcrevrrr rmvqgktrrr 181 sstthvkqai nkmltkiss
```

Ref Seq ID: NP_001177655.1
RERG (isoform 2)

SEQ ID NO: 4

```
  1 maksaevkla ifgragvgks estyrhqati ddevvsmeil dtagqedtiq reghmrwgeg 61 fvlvyditdr gsfeevlplk nildeikkpk nvtlilvgnk adldhsrqvs teegeklate 121 lacafyecsa ctgegnitei fyelcrevrr rrmvqgktrr rsstthvkqa inkmltkiss
```

---

The invention claimed is:

1. A method of treating a subject with mesothelioma, comprising administering a composition comprising an effective amount of an estrogen or an estrogen mimetic to the subject when a biological sample from the subject has been determined to have an Ras-like, estrogen-regulated, growth inhibitor (RERG) expression level below a reference level, wherein the reference level is an average REGR protein or gene product level in a comparable biological sample from a population of mesothelioma subjects with a median overall survival time after surgery for mesothelioma.

2. The method of claim 1, wherein the mesothelioma is malignant mesothelioma.

3. The method of claim 2, wherein the malignant mesothelioma is malignant plural mesothelioma (MPM).

4. The method of claim 1, further comprising selecting the subject to be treated before onset of said administering, comprising assaying a biological sample from the subject for the expression of the Ras-like, estrogen-regulated, growth inhibitor (RERG) protein or the RERG gene product, and selecting the subject where the expression of the RERG protein or gene product is at the same level or above a reference level for RERG protein or gene product.

5. The method of claim 1, wherein the estrogen mimetic is an estrogen-like agent which has a similar biological function to estrogen.

6. The method of claim 1, wherein the estrogen is a natural or synthetic estrogen.

7. The method of claim 1, wherein the estrogen is selected from the group consisting of estradiol, estrone, estriol, 17α-estradiol, 17β-estradiol.

8. The method of claim 1, wherein the estrogen mimetic is selected from the group consisting of: 2-fluoro-3,17β-estradiol, 2,4-difluoro-3,17β-estradiol, 2-fluoroestrone, 2,4-difluoroestrone, 2-fluoro-17α-ethinyl-3,17β.-estradiol, 2,4-difluoro-17α-ethinyl-3,17β-estradiol, 2-fluoro-17α-ethinylestradiol 3-methyl ether, 2,4-difluoro-17α-ethinylestradiol 3-methyl ether, 15.βH,3'H-cycloprop[14,15]-estra-1,3,5(10),8-tetraen-3,17α-diol, 5.βH,3'H-cycloprop[14,15]-18α-homoestra-1,3,5(10),8-tetraen-3,17α-diol, 17α-hydroxy-15βH,3'H-cycloprop[14,15]-estra-1,3,5(10),8-tetraen-3-yl-pentanoate, 17-methylene-15βH, 3'H-cycloprop[14,15]-estra-1,3,5(10),8-tetraen-3-ol, 15βH,3'H-3',3'-difluorocycloprop[14,15]-estra-1,3,5(10),8-tetraen-3,17α-diol, 17-methylene-15βH,3'H-cycloprop[14,15]-estra-1,3,5(10),8-tetraen-3-yl-sulfamate, 17-difluoromethylene-15βH,3'H-cycloprop[14,15]-estra-1,3,5(10),8-tetra en-3-ol, 3-methoxy-15β-methyl-3'H-cycloprop[14,15]-estra-1,3,5(10),8-tetraen-3-ol, 15α-methyl-3'H-cycloprop[14,15]-estra-1,3,5(10),8-tetraen-3,17α-diol, 17-difluoromethylene-15βH,3'H-cycloprop[14,15]-estra-1,3,5(10),8-tetra en-3-yl-(tetramethylenimino)sulfonate and 17-methylene-3'H-cycloprop[8,9]-15.beta.H,3'H-cycloprop[14,15]-estra-1,3,5(10)-trien-3-ol.

9. The method of claim 1, wherein the biological sample comprises a biopsy sample, blood sample, plasma sample, urine sample.

10. The method of claim 1, further comprising administering an additional therapeutic agent to the subject.

11. The method of claim 10, wherein the additional therapeutic agent is a chemotherapeutic agent or an agent used to treat mesothelioma.

12. The method of claim 11, wherein an agent used to treat mesothelioma is selected from the group consisting of pemetrexed, cisplatin and carboplatin.

13. A method of treating a subject with mesothelioma, comprising:
(a) assaying a biological sample from the subject for the expression of the Ras-like, estrogen-regulated, growth inhibitor (RERG) protein or the RERG gene product; and
(b) administering a composition comprising an effective amount of an estrogen or an estrogen mimetic to the subject when the biological sample from the subject has been determined to have an Ras-like, estrogen-regulated, growth inhibitor (RERG) expression level below a reference level, wherein the reference level is an average REGR protein or gene product level in a comparable biological sample from a population of mesothelioma subjects with a median overall survival time after surgery for mesothelioma.

14. The method of claim 13, wherein the mesothelioma is malignant mesothelioma.

15. The method of claim 14, wherein the malignant mesothelioma is malignant plural mesothelioma (MPM).

16. The method of claim 13, wherein the estrogen mimetic is an estrogen-like agent which has a similar biological function to estrogen.

17. The method of claim 13, wherein the estrogen is a natural or synthetic estrogen.

18. The method of claim 13, wherein the estrogen is selected from the group consisting of estradiol, estrone, estriol, 17α-estradiol, 17β-estradiol.

19. The method of claim 13, wherein the estrogen mimetic is selected from the group consisting of: 2-fluoro-3,17β-estradiol, 2,4-difluoro-3,17β-estradiol, 2-fluoroestrone, 2,4-difluoroestrone, 2-fluoro-17α-ethinyl-3,17β.-estradiol, 2,4-difluoro-17α-ethinyl-3,17β-estradiol, 2-fluoro-17α-ethinylestradiol 3-methyl ether, 2,4-difluoro-17α-ethinylestradiol 3-methyl ether, 15.βH,3'H-cycloprop[14,15]-estra-1,3,5(10),8-tetraen-3,17α-diol, 5.βH,3'H-cycloprop[14,15]-18α-homoestra-1,3,5(10),8-tetraen-3,17α-diol, 17α-hydroxy-15βH,3'H-cycloprop[14,15]-estra-1,3,5(10),8-tetraen-3-yl-pentanoate, 17-methylene-15βH,3'H-cycloprop[14,15]-estra-1,3,5(10),8-tetraen-3-ol, 15βH,3'H-3',3'-difluorocycloprop[14,15]-estra-1,3,5(10),8-tetraen-3,17α-diol, 17-methylene-15βH,3'H-cycloprop[14,15]-estra-1,3,5(10),8-tetraen-3-yl-sulfamate, 17-difluoromethylene-15βH,3'H-cycloprop[14,15]-estra-1,3,5(10),8-tetra en-3-ol, 3-methoxy-15β-methyl-3'H-cycloprop[14,15]-estra-1,3,5(10),8-tetraen-3-ol, 15α-methyl-3'H-cycloprop[14,15]-estra-1,3,5(10),8-tetraen-3,17α-diol, 17-difluoromethylene-15βH,3'H-cycloprop[14,15]-estra-1,3,5(10),8-tetra en-3-yl-(tetramethylenimino)sulfonate and 17-methylene-3'H-cycloprop[8,9]-15.beta.H,3'H-cycloprop[14,15]-estra-1,3,5(10)-trien-3-ol.

20. The method of claim 13, wherein the biological sample comprises a biopsy sample, blood sample, plasma sample, urine sample.

21. The method of claim 13, further comprising administering an additional therapeutic agent to the subject.

22. The method of claim 21, wherein the additional therapeutic agent is a chemotherapeutic agent or an agent used to treat mesothelioma.

23. The method of claim 22, wherein an agent used to treat mesothelioma is selected from the group consisting of pemetrexed, cisplatin and carboplatin.

* * * * *